(12) United States Patent
Hosaka et al.

(10) Patent No.: US 8,323,905 B2
(45) Date of Patent: Dec. 4, 2012

(54) METHODS OF DETECTION GPVI

(75) Inventors: Yoshitaka Hosaka, Tokyo (JP); Katsuki Naitoh, Tokyo (JP); Motoyasu Honda, Tokyo (JP)

(73) Assignee: Mochida Pharmaceutical Co., Ltd., Tokyo (JP)

( * ) Notice: Subject to any disclaimer, the term of this patent is extended or adjusted under 35 U.S.C. 154(b) by 337 days.

(21) Appl. No.: 12/225,722

(22) PCT Filed: Mar. 20, 2007

(86) PCT No.: PCT/JP2007/056530
§ 371 (c)(1),
(2), (4) Date: Nov. 10, 2008

(87) PCT Pub. No.: WO2007/116779
PCT Pub. Date: Oct. 18, 2007

(65) Prior Publication Data
US 2009/0311728 A1    Dec. 17, 2009

(30) Foreign Application Priority Data

Mar. 31, 2006    (JP) ................................. 2006-100241

(51) Int. Cl.
  *G01N 33/53* (2006.01)
(52) U.S. Cl. ...... 435/7.1; 435/7.21; 435/7.92; 435/7.94; 530/388.1; 530/388.25; 514/13.7; 514/13.8
(58) Field of Classification Search ........................ None
See application file for complete search history.

(56) References Cited

U.S. PATENT DOCUMENTS

| 6,998,469 | B2 | 2/2006 | Tandon et al. |
| 7,645,592 | B2 | 1/2010 | Takizawa et al. |
| 2003/0186885 | A1 | 10/2003 | Tandon et al. |
| 2004/0001826 | A1 | 1/2004 | Gill et al. |
| 2006/0088531 | A1 | 4/2006 | Smethurst et al. |
| 2007/0025992 | A1 | 2/2007 | Takayama et al. |
| 2007/0071744 | A1 | 3/2007 | Munch et al. |
| 2007/0202108 | A1 | 8/2007 | Tandon et al. |
| 2007/0207155 | A1 | 9/2007 | Takizawa et al. |
| 2009/0092612 | A1* | 4/2009 | Takayama et al. ......... 424/139.1 |
| 2009/0130021 | A1 | 5/2009 | Munch et al. |

FOREIGN PATENT DOCUMENTS

| EP | 1 224 942 A1 | 7/2002 |
| WO | WO 02080968 A1 * | 10/2002 |
| WO | WO 03/054020 A2 | 7/2003 |
| WO | WO 2005/007800 A2 | 1/2005 |
| WO | WO 2005/054294 A2 | 6/2005 |
| WO | WO 2005/111083 A2 | 11/2005 |
| WO | WO 2006/061650 A2 | 6/2006 |
| WO | WO 2006118350 A1 * | 11/2006 |
| WO | WO 2006/131512 A2 | 12/2006 |

OTHER PUBLICATIONS

Douville et al., Genomics. Oct. 1992;14(2):503-5, abstract only.*
Lindl et al., J Neuroimmune Pharmacol. Sep. 2010;5(3):294-309. Epub Apr. 16, 2010.*
Badreldin et al., Interact Cardiovasc Thorac Surg. May 2010;10(5):766-9. Epub Feb. 12, 2010.*
Boylan et al., "Anti-GPVI-associated ITP: an acquired platelet disorder caused by autoantibody-mediated clearance of the GPVI/FcRγ-chain complex from the human platelet surface," Blood, Sep. 1, 2004, 104(5):1350-1355.
Gardiner et al., "Regulation of platelet membrane levels of glycoprotein VI by a platelet-derived metalloproteinase," Blood, Dec. 1, 2004, 104(12):3611-3617.
Supplementary European Search Report dated Mar. 13, 2009, in corresponding European Application 07739968, 7 pages.
Moroi et al., "Platelet glycoprotein VI: its structure and function," Thrombosis Research, 2004, 114:221-233.

* cited by examiner

*Primary Examiner* — Michael Szperka
(74) *Attorney, Agent, or Firm* — Foley & Lardner LLP

(57) ABSTRACT

The present invention provides a convenient and highly sensitive method of determining sGPVI present in plasma; this is accomplished by establishing a plurality of mouse hybridomas that produce antibody against GPVI and combining the antibodies produced therefrom. Provided thereby are a novel platelet activation marker, a reagent and method for determining this novel platelet activation marker, and novel applications of this marker in, for example, the diagnosis of diseases associated with platelet activation/vascular endothelial injury.

11 Claims, 24 Drawing Sheets

Fig.1

```
  1 ATGTCTCCAGCCTCACTCACTTTCTTCTGTATTGGGCTGTGTGTACTACAAGTGATCCAA   60
    METSerProAlaSerLeuThrPhePheCysIleGlyLeuCysValLeuGlnValIleGln

61 GCACAGCATGGCCCACTCCCCAAGCCTTCTCTCCAGGCTCAACCCAGTTCCCTGGTGCCC  120
    AlaGlnHisGlyProLeuProLysProSerLeuGlnAlaGlnProSerSerLeuValPro

121 CTGGGTCATCCAGTCACTCTGAGGTGCCTGGGGCCTTCAGATGCGGATTTATATCGTCTG  180
    LeuGlyHisProValThrLeuArgCysLeuGlyProSerAspAlaAspLeuTyrArgLeu

181 GAGAAAGTGAAACCCGGGAAGTTGATCTTCATAGATCAAGACTTTCTCTTCATTCCAATC  240
    GluLysValLysProGlyLysLeuIlePheIleAspGlnAspPheLeuPheIleProIle

241 ATGGAAATAAATAATGCTGGACGCTACCGCTGCTCATATCAGAATGAGAGTCATTGGTCT  300
    METGluIleAsnAsnAlaGlyArgTyrArgCysSerTyrGlnAsnGluSerHisTrpSer

301 CTCCCAAGTGACCAGCTTGAGCTAATTGCTACAGGTGTTTACTCTAAGCCCTCACTTTCA  360
    LeuProSerAspGlnLeuGluLeuIleAlaThrGlyValTyrSerLysProSerLeuSer

361 GCTCATCCCAGCTCAGCAATCCCTCCAGGCAGGGATGTGACTCTGAAGTGCCAAAGCCAA  420
    AlaHisProSerSerAlaIleProProGlyArgAspValThrLeuLysCysGlnSerGln

421 TATAGTTTTGACGAATTTGTTTTATACAAAGAGGGGGATACTAGGCCTTATAAGAGACCT  480
    TyrSerPheAspGluPheValLeuTyrLysGluGlyAspThrArgProTyrLysArgPro

481 GAGAAATGGTACCGGGCCAATTTCCCCGTCATCACAGTGACTGCTGCTCACAGTGGGACT  540
    GluLysTrpTyrArgAlaAsnPheProValIleThrValThrAlaAlaHisSerGlyThr

541 TACCGGTGTTACAGCTTTTCCAGCTCATCTCCATACCTGTGGTCAGCACCGAGTGACCCT  600
    TyrArgCysTyrSerPheSerSerSerSerProTyrLeuTrpSerAlaProSerAspPro

601 CTAGTAGTTGTGGTTACTGGACCCTCTGCCACTCCCAGTCAGGTACCCACAGAGGTACCA  660
    LeuValValValValThrGlyProSerAlaThrProSerGlnValProThrGluValPro

661 TCTCCTATGACAGAAGCCTCCAGGAGACCTTCCATGTTACTCACAAACAAAATATCTACA  720
    SerProMETThrGluAlaSerArgArgProSerMETLeuLeuThrAsnLysIleSerThr

721 ACTGAAAAGCCTATGAATATCACTGTCTCTCCAGAGGGGCCAAGCCCTCCATTTGGTTTT  780
    ThrGluLysProMETAsnIleThrValSerProGluGlyProSerProProPheGlyPhe

781 GCTCATCAGCACTATGCCAAGGGGAATCTGGTCCGGATATGCCTTGGTGTCATGATTATA  840
    AlaHisGlnHisTyrAlaLysGlyAsnLeuValArgIleCysLeuGlyValMETIleIle

841 ATGTTCTTGGTGGGGTTTCTGGCAGAGGATTGGCACAGTCGGAAGAAACGCCTACAACAC  900
    METPheLeuValGlyPheLeuAlaGluAspTrpHisSerArgLysLysArgLeuGlnHis

901 AGGATCAGAGCTATGCAAAGGCCACTGCCACCTCTCCCACTGGCCTAG  948
    ArgIleArgAlaMETGlnArgProLeuProProLeuProLeuAla***
```

Fig.2

```
                                  Domain 1
    1 : QSGPLPKPSL QALPSSLVPL EKPVTLRCQG PPGVDLYRLE KLSSSR--YQ DQAVLFIPAM
        * ******** ** ******  ****** * *  ****** *     **  *** *
    1 : QHGPLPKPSL QAQPSSLVPL GHPVTLRCLG PSDADLYRLE KVKPGKLIFI DQDFLFIPIM
           L1         L2          L3          L4          L5

59 : KRSLAGRYRC SYQNGSLWSL PSDQLELVAT GVFAKPSLSA QPGPAVSSGG DVTLQCQTRY
        ******  **** *  *** ******* **  **  ******   *   *   **** **   *
   61 : EINNAGRYRC SYQNESHWSL PSDQLELIAT GVYSKPSLSA HPSSAIPPGR DVTLKCQSQY
           L6         L7          L8          L9
                                  Domain 2
  119 : GFDQFALYKE GDPAPYKNPE RWYRASFPII TVTAAHSGTY RCYSFSSRDP YLWSAPSDPL
        ** * **** **   *** ** ****  ** * ********** *******  * **********
  121 : SFDEFVLYKE GDTRPYKRPE KWYRANFPVI TVTAAHSGTY RCYSFSSSSP YLWSAPSDPL
           L10        L11         L12         L13
                                  Domain 3
  179 : ELVVTGTSVT PSRLPTEPPS SVAEFSEATA ELTVSFTNKV FTTETSRSIT TSPKESDSPA
        ****  *  ** ***  **   * *    *   ***    *** ***   **  **        *
  181 : VVVVTGPSAT PSQVPTEVPS PMTEASRRPS ML---LTNKI STTEKPMNIT VSPEGPSPPF
           L14

239 : GPARQYYTKG N    ; Human
        * * * ** *
  238 : GFAHQHYAKG N    ; Rat
```

Fig.3

Domain 1

```
  1 : QSGPLPKPSL QALPSSLVPL EKPVTLRCQG PPGVDLYRLE KESSSRYQDQ AVLFIPAMKR
      ********** ** ******* *  *****  ** ******* **   * **  **** * *
  1 : QSGPLPKPSL QAQPSSLVPL GQSVILRCQG PPDVDLYRLE KEKPEKYEDQ DFLFIPTMER
          L1         L2         L3         L4         L5

61 : SLAGRYRCSY QNGSLWSLPS DQLELVATGV FAKPSLSAQP GPAVSSGGDV TLQCQTRYGF
      * ******** **** ***** ***** ****  ******* *  **  * ** ** **  * *
 61 : SNAGRYRCSY QNGSHWSLPS DQLELIATGV YAKPSLSAHP SSAVPQGRDV TLKCQSPYSF
          L6         L7         L8         L9
```

Domain 2

```
121 : DQFALYKEGD PAPYKNPERW YRASFPIITV TAAHSGTYRC YSFSSRDPYL WSAPSDPLEL
      * * ****** ** ** * ** ** ****** ********** ****  ***  ******** *
121 : DEFVLYKEGD TGSYKRPEKW YRANFPIITV TAAHSGTYRC YSFSSSSPYL WSAPSDPLVL
          L10        L11        L12        L13        L14
```

Domain 3

```
181 : VVTGTSVTPS RLPTEPPSSV AEFSEATAEL TVSFTNKVFT TETSRSITTS PKESDSPAGP
      ****  * *** ***   * *   *     *   *** *  ** ** *  *  *   *  * *
181 : VVTGLSATPS QVPTEESFPV TESSRRPSIL ---PTNKIST TEKPMNITAS PEGLSPPFGF
```

```
241 : ARQYYTKGN       ; Human
      *  *  ***
238 : AHQHYAKGN       ; Mouse
```

Lane 1: Molecular weight markers
Lane 2: Recombinant rat GPVI-hFc
Lane 3: Recombinant rat GPVI-mFc Lane 1: Molecular weight markers
Lane 2: F1239-6-1

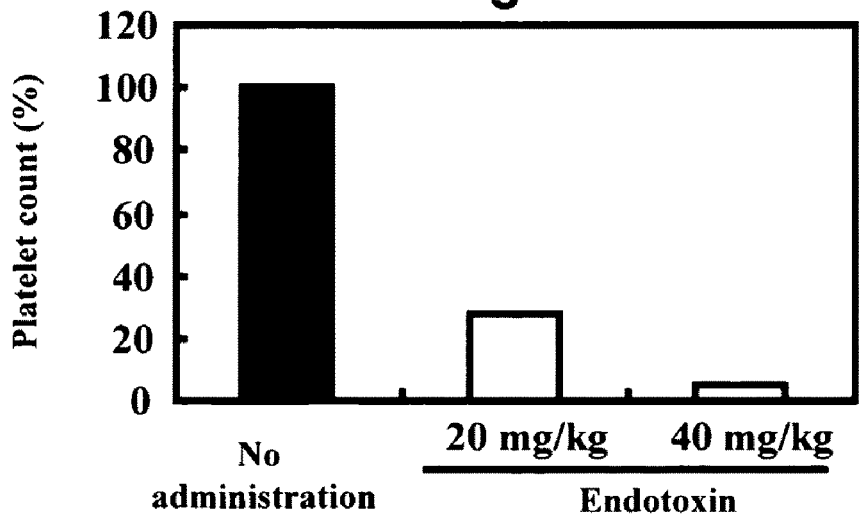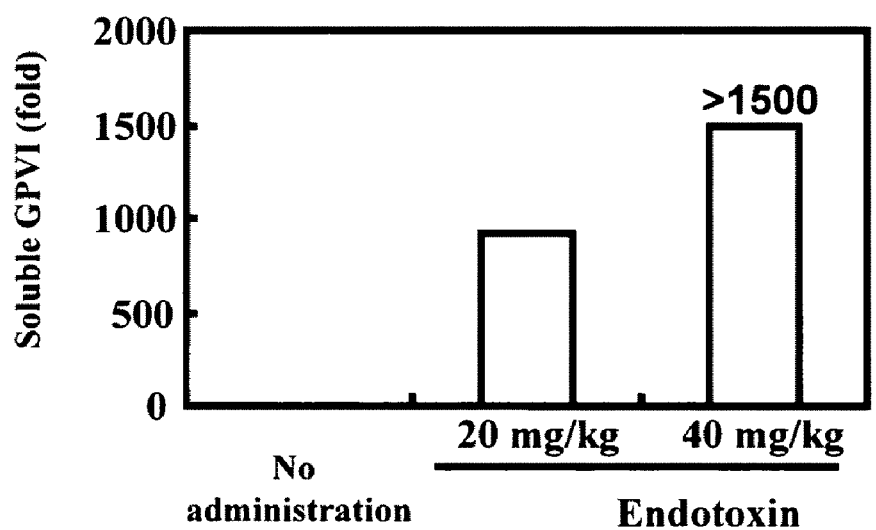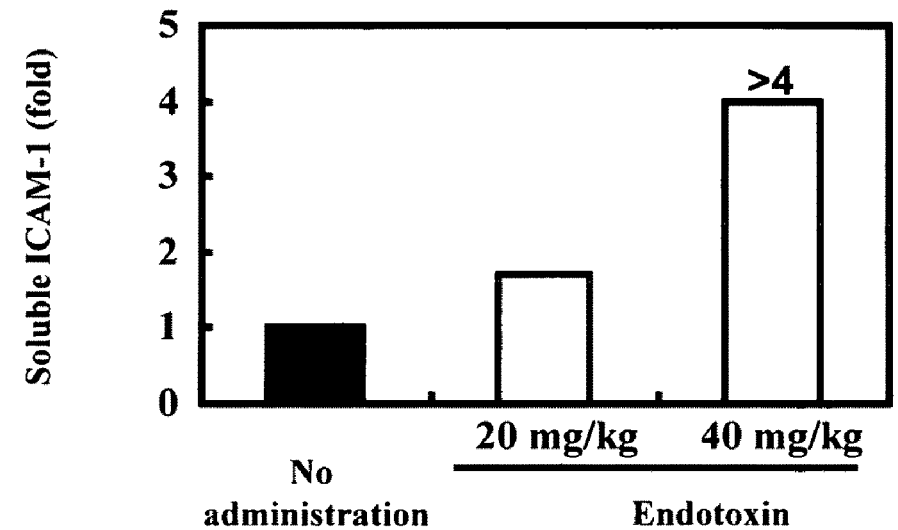
Fig.17

Fig.18 (A)
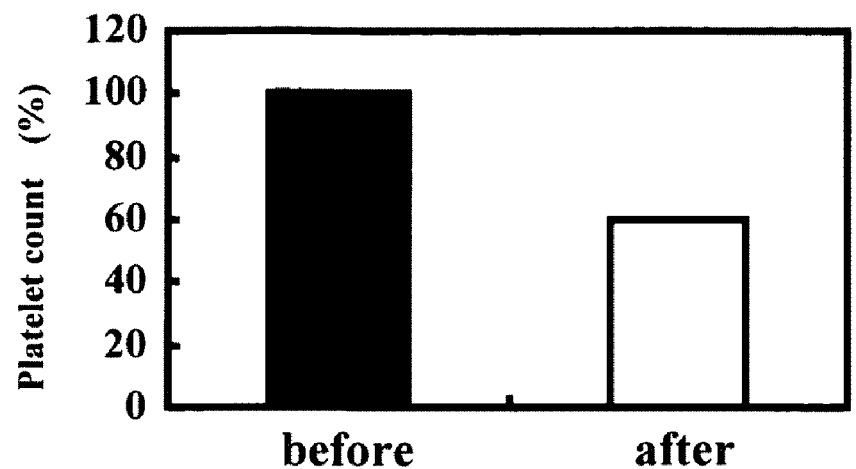
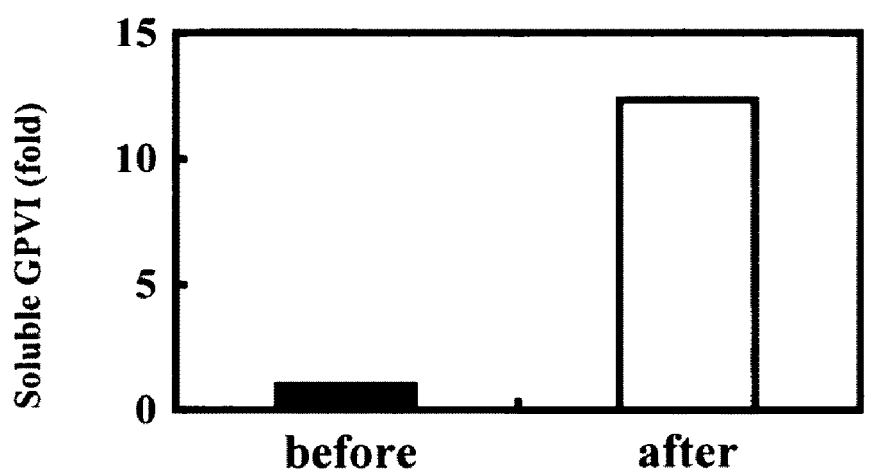
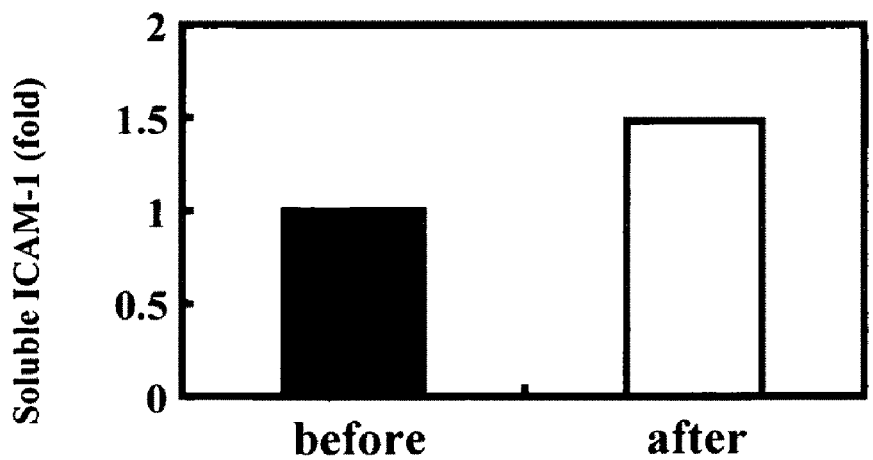

Fig.19 (A)
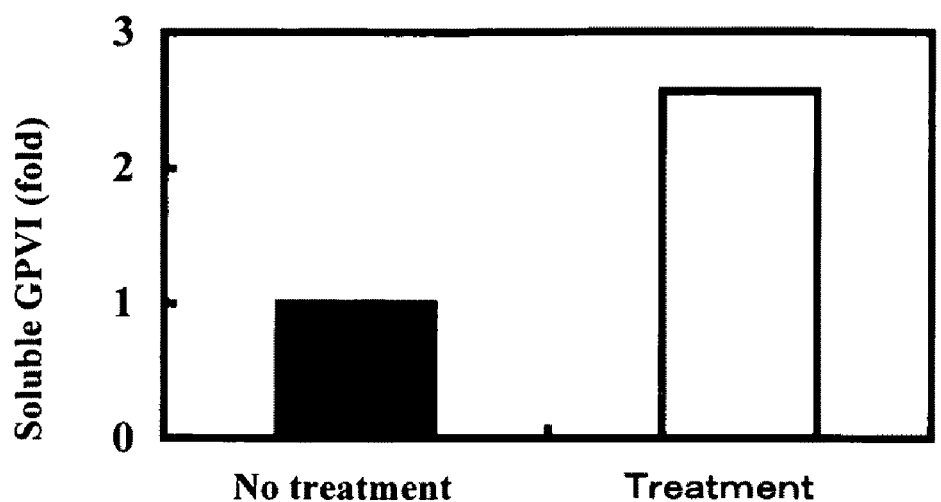
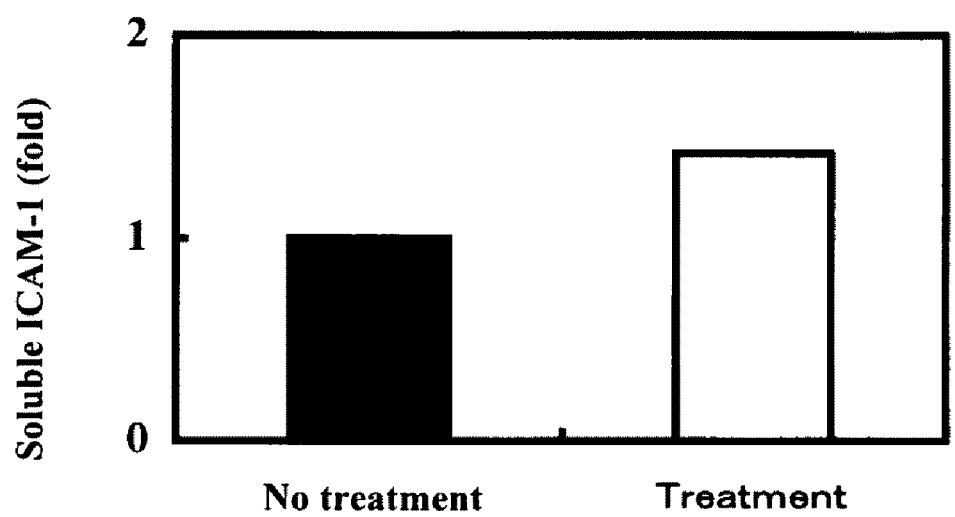

Fig.22

F1232-7-1 Detection

| | Buffer | Convulxin 0.15 μg/mL |
|---|---|---|
| Supernatant sGPVI | | |

F1232-10-2 Detection

| | Buffer | Convulxin 0.15 μg/mL |
|---|---|---|
| Supernatant sGPVI | | |

Polyclonal Antibody Detection

| | Buffer | Convulxin 0.15 μg/mL |
|---|---|---|
| Supernatant sGPVI | | |

SEQUENCE LISTING

```
<160> NUMBER OF SEQ ID NOS: 25

<210> SEQ ID NO 1
<211> LENGTH: 23
<212> TYPE: DNA
<213> ORGANISM: Artificial
<220> FEATURE:
<223> OTHER INFORMATION: primer

<400> SEQUENCE: 1
ccctcagcgc atcctgttcc tat                                              23

<210> SEQ ID NO 2
<211> LENGTH: 23
<212> TYPE: DNA
<213> ORGANISM: Artificial
<220> FEATURE:
<223> OTHER INFORMATION: primer

<400> SEQUENCE: 2
tttcccaggt caccttcagg act                                              23

<210> SEQ ID NO 3
<211> LENGTH: 22
<212> TYPE: DNA
<213> ORGANISM: Artificial
<220> FEATURE:
<223> OTHER INFORMATION: primer

<400> SEQUENCE: 3
ttaagggagt ctctagcctc tg                                               22

<210> SEQ ID NO 4
<211> LENGTH: 30
<212> TYPE: DNA
<213> ORGANISM: Artificial
<220> FEATURE:
<223> OTHER INFORMATION: primer

<400> SEQUENCE: 4
gtttagcata cacacctgta gcaattagct                                       30

<210> SEQ ID NO 5
<211> LENGTH: 23
<212> TYPE: DNA
<213> ORGANISM: Artificial
<220> FEATURE:
<223> OTHER INFORMATION: primer

<400> SEQUENCE: 5
cctgtttcct gtctttaata gag                                              23

<210> SEQ ID NO 6
<211> LENGTH: 22
```

-continued

```
<212> TYPE: DNA
<213> ORGANISM: Artificial
<220> FEATURE:
<223> OTHER INFORMATION: primer

<400> SEQUENCE: 6
ccttgcccac acctctgact cc                                              22

<210> SEQ ID NO 7
<211> LENGTH: 25
<212> TYPE: DNA
<213> ORGANISM: Artificial
<220> FEATURE:
<223> OTHER INFORMATION: primer

<400> SEQUENCE: 7
gtgagaaaat caagtcacag aaatg                                           25

<210> SEQ ID NO 8
<211> LENGTH: 23
<212> TYPE: DNA
<213> ORGANISM: Artificial
<220> FEATURE:
<223> OTHER INFORMATION: primer

<400> SEQUENCE: 8
ttcagacaca tttgtagtag aac                                             23

<210> SEQ ID NO 9
<211> LENGTH: 23
<212> TYPE: DNA
<213> ORGANISM: Artificial
<220> FEATURE:
<223> OTHER INFORMATION: primer

<400> SEQUENCE: 9
ggagcacttg ggatgaactg tca                                             23

<210> SEQ ID NO 10
<211> LENGTH: 22
<212> TYPE: DNA
<213> ORGANISM: Artificial
<220> FEATURE:
<223> OTHER INFORMATION: primer

<400> SEQUENCE: 10
gagaaaccca tcctcttgcc ac                                              22

<210> SEQ ID NO 11
<211> LENGTH: 24
<212> TYPE: DNA
<213> ORGANISM: Artificial
<220> FEATURE:
<223> OTHER INFORMATION: primer

<400> SEQUENCE: 11
gcttcacaag catatgagca cgtg                                            24

<210> SEQ ID NO 12
<211> LENGTH: 23
<212> TYPE: DNA
<213> ORGANISM: Artificial
<220> FEATURE:
<223> OTHER INFORMATION: primer

<400> SEQUENCE: 12
attatagctc tatagattcc atg                                             23
```

```
<210> SEQ ID NO 13
<211> LENGTH: 27
<212> TYPE: DNA
<213> ORGANISM: Artificial
<220> FEATURE:
<223> OTHER INFORMATION: primer

<400> SEQUENCE: 13
gggaattcca tgtctccagc ctcactc                                         27

<210> SEQ ID NO 14
<211> LENGTH: 23
<212> TYPE: DNA
<213> ORGANISM: Artificial
<220> FEATURE:
<223> OTHER INFORMATION: primer

<400> SEQUENCE: 14
ccaagttatt tctaggccag tgg                                             23

<210> SEQ ID NO 15
<211> LENGTH: 30
<212> TYPE: DNA
<213> ORGANISM: Artificial
<220> FEATURE:
<223> OTHER INFORMATION: primer

<400> SEQUENCE: 15
ccaggagttc aggtgctggg cacggtgggc                                      30

<210> SEQ ID NO 16
<211> LENGTH: 30
<212> TYPE: DNA
<213> ORGANISM: Artificial
<220> FEATURE:
<223> OTHER INFORMATION: primer

<400> SEQUENCE: 16
gtggttactg daccctctgc cactcccagc                                      30

<210> SEQ ID NO 17
<211> LENGTH: 30
<212> TYPE: DNA
<213> ORGANISM: Artificial
<220> FEATURE:
<223> OTHER INFORMATION: primer

<400> SEQUENCE: 17
gctgggagtg gcagagggtc cagtaaccac                                      30

<210> SEQ ID NO 18
<211> LENGTH: 360
<212> TYPE: DNA
<213> ORGANISM: Mus musculus

<400> SEQUENCE: 18
gtccagctgc agcagtctgg gcctgagctg gtgaggcctg gggaatcagt gaagatttcc     60
tgcaagggtt ccggctacac attcactgat tatgctatac actgggtgaa gctgagtcat    120
gcaaagagtc tagagtggat tggagttatt agtatttact atgatgatac aaactacaac    180
cagaagttta agggcaaggc cacaatgact gtagacaaat cctccagcac agcctatctg    240
gaacttgcca gattgacatc tgaggattct gccatctatt actgtgcaag acgaagggac    300
agctcgggtc cctatgctat ggactactgg ggtcaaggaa cctcagtcac cgtctcctca    360
```

<210> SEQ ID NO 19
<211> LENGTH: 348
<212> TYPE: DNA
<213> ORGANISM: Mus musculus

<400> SEQUENCE: 19

```
gacattgtgc tgacccaatc tccagcttct ttggctgtgt ctctagggca gagggccacc    60
atatcctgca gagccagtga agtgttgat agttatggca atagttttat gcactggtac   120
cagcagaaac caggacagcc acccaaactc ctcatctatc gtgcatccaa cctagaatct   180
gggatccctg ccaggttcag tggcagtggg tctaggacag acttcaccct caccattaat   240
cctgtggagg ctgatgatgt tgcaacctat tactgtcagc aaagtaatga ggatccgtac   300
acgttcggag gggggaccaa gctggaaata aaacgggctg atgctgca                 348
```

<210> SEQ ID NO 20
<211> LENGTH: 120
<212> TYPE: PRT
<213> ORGANISM: Mus musculus

<400> SEQUENCE: 20

```
Val Gln Leu Gln Gln Ser Gly Pro Glu Leu Val Arg Pro Gly Glu Ser
1               5                   10                  15
Val Lys Ile Ser Cys Lys Gly Ser Gly Tyr Thr Phe Thr Asp Tyr Ala
                20                  25                  30
Ile His Trp Val Lys Leu Ser His Ala Lys Ser Leu Glu Trp Ile Gly
            35                  40                  45
Val Ile Ser Ile Tyr Tyr Asp Asp Thr Asn Tyr Asn Gln Lys Phe Lys
        50                  55                  60
Gly Lys Ala Thr Met Thr Val Asp Lys Ser Ser Ser Thr Ala Tyr Leu
65                  70                  75                  80
Glu Leu Ala Arg Leu Thr Ser Glu Asp Ser Ala Ile Tyr Tyr Cys Ala
                85                  90                  95
Arg Arg Arg Asp Ser Ser Gly Pro Tyr Ala Met Asp Tyr Trp Gly Gln
            100                 105                 110
Gly Thr Ser Val Thr Val Ser Ser
        115                 120
```

<210> SEQ ID NO 21
<211> LENGTH: 116
<212> TYPE: PRT
<213> ORGANISM: Mus musculus

<400> SEQUENCE: 21

```
Asp Ile Val Leu Thr Gln Ser Pro Ala Ser Leu Ala Val Ser Leu Gly
1               5                   10                  15
Gln Arg Ala Thr Ile Ser Cys Arg Ala Ser Glu Ser Val Asp Ser Tyr
                20                  25                  30
Gly Asn Ser Phe Met His Trp Tyr Gln Gln Lys Pro Gly Gln Pro Pro
            35                  40                  45
Lys Leu Leu Ile Tyr Arg Ala Ser Asn Leu Glu Ser Gly Ile Pro Ala
        50                  55                  60
Arg Phe Ser Gly Ser Gly Ser Arg Thr Asp Phe Thr Leu Thr Ile Asn
65                  70                  75                  80
Pro Val Glu Ala Asp Asp Val Ala Thr Tyr Tyr Cys Gln Gln Ser Asn
                85                  90                  95
Glu Asp Pro Tyr Thr Phe Gly Gly Gly Thr Lys Leu Glu Ile Lys Arg
```

Ala Asp Ala Ala
        115

<210> SEQ ID NO 22
<211> LENGTH: 357
<212> TYPE: DNA
<213> ORGANISM: Mus musculus

<400> SEQUENCE: 22
gttactctga aagagtctgg ccctgggata ttgcagccct cccagaccct cagtctgact      60
tgttctttct ctgggttttc actgagcact tatggtatag agtaggctg gattcgtcag     120 ccttcaggga agggtctgga gtggctggca cacatttggt ggaatgatga taagtactat    180
aacacagccc tgaagagccg gctcacaatc tccaaggata cctccaacaa ccaggtattc    240
ctcaagatcg ccagtgtgga cactgcagac actgccacat actactgtgc tcgagtttat    300
tactacggta gtagttttga ctactggggc caaggcacca ctctcacagt ctcctca       357

<210> SEQ ID NO 23
<211> LENGTH: 336
<212> TYPE: DNA
<213> ORGANISM: Mus musculus

<400> SEQUENCE: 23
gacatccaga tgactcagtc tccagcctcc ctatctgcat ctgtgggaga aactgtcacc     60
atcacatgtc gagcaagtga gaatatttc agtattttag catggtatca gcagaaacag    120
ggaaaatctc ctcaactcct ggtctatgct gcaacaaatt tagcagatgg tgtgccatca    180
aggttcagtg gcagtggatc aggcacacag ttttctctga agatcaacag cctgcagcct    240
gaagattttg ggagttatta ctgtcaacat ttttatggta ctccgtggac gttcggtgga    300
ggcaccaagc tggaaatcaa acgggctgat gctgca                              336

<210> SEQ ID NO 24
<211> LENGTH: 119
<212> TYPE: PRT
<213> ORGANISM: Mus musculus

<400> SEQUENCE: 24

Val Thr Leu Lys Glu Ser Gly Pro Gly Ile Leu Gln Pro Ser Gln Thr
1               5                   10                  15

Leu Ser Leu Thr Cys Ser Phe Ser Gly Phe Ser Leu Thr Tyr Gly
            20                  25                  30

Ile Gly Val Gly Trp Ile Arg Gln Pro Ser Gly Lys Gly Leu Glu Trp
        35                  40                  45

Leu Ala His Ile Trp Trp Asn Asp Asp Lys Tyr Tyr Asn Thr Ala Leu
    50                  55                  60

Lys Ser Arg Leu Thr Ile Ser Lys Asp Thr Ser Asn Asn Gln Val Phe
65                  70                  75                  80

Leu Lys Ile Ala Ser Val Asp Thr Ala Asp Thr Ala Thr Tyr Tyr Cys
                85                  90                  95

Ala Arg Val Tyr Tyr Tyr Gly Ser Ser Phe Asp Tyr Trp Gly Gln Gly
            100                 105                 110

Thr Thr Leu Thr Val Ser Ser
        115

<210> SEQ ID NO 25
<211> LENGTH: 112

```
<212> TYPE: PRT
<213> ORGANISM: Mus musculus

<400> SEQUENCE: 25

Asp Ile Gln Met Thr Gln Ser Pro Ala Ser Leu Ser Ala Ser Val Gly
1               5                   10                  15

Glu Thr Val Thr Ile Thr Cys Arg Ala Ser Glu Asn Ile Phe Ser Ile
            20                  25                  30

Leu Ala Trp Tyr Gln Gln Lys Gln Gly Lys Ser Pro Gln Leu Leu Val
        35                  40                  45

Tyr Ala Ala Thr Asn Leu Ala Asp Gly Val Pro Ser Arg Phe Ser Gly
    50                  55                  60

Ser Gly Ser Gly Thr Gln Phe Ser Leu Lys Ile Asn Ser Leu Gln Pro
65                  70                  75                  80

Glu Asp Phe Gly Ser Tyr Tyr Cys Gln His Phe Tyr Gly Thr Pro Trp
                85                  90                  95

Thr Phe Gly Gly Gly Thr Lys Leu Glu Ile Lys Arg Ala Asp Ala Ala
                100                 105                 110
```

METHODS OF DETECTION GPVI

This application is a National Stage application of PCT/JP2007/056530, filed Mar. 20, 2007, which claims priority from Japanese application JP 2006-100241, filed Mar. 31, 2006.

TECHNICAL FIELD

The present invention relates to a novel platelet activation marker, a reagent and method for determining this novel platelet activation marker, and novel applications of the marker to the diagnosis of diseases associated with platelet activation/vascular endothelial injury.

BACKGROUND OF THE INVENTION

The leading cause of death in Japan is malignant neoplasm, while the second leading cause is heart disease and the third leading cause is cerebrovascular disease. The majority of heart disease and cerebrovascular disease is accounted for by thrombosis, such as myocardial infarction and cerebral infarction, and together the two of these rival the number of deaths from cancer. The prevention and treatment of thrombosis continues to be an important issue. Controlling platelet activation is crucial for the prevention and treatment of thrombosis, and antiplatelet drugs are aggressively prescribed. However, the clinical efficacy have by no means come up to satisfactory levels.

Platelet function can be divided into two reactions: adhesion to subendothelial tissue at a site of vascular injury, and aggregation, in which the platelets adhere to one another. In particular, the latter is accompanied by the release of the contents of granules that are present in platelets. In addition, various molecules participate in the expression of function in the platelet activation process, and these are utilized as platelet activation markers. The effective utilization of these markers not only enables greater clarity in the diagnosis of abnormal thrombosis, but also enables a more appropriate selection of the treatment protocol.

The determination of β-thromboglobulin and platelet factor 4, which are stored in the α-granules of platelets, has been carried out in the past as an indicator of platelet activation. However, these require consideration from the influence of the blood sampling technique and the fact that they assume high values when renal function declines, and thus they are not always categorized as an appropriate markers. Moreover, in the case of high value of both β-thromboglobulin and platelet factor 4, it must be treated with caution due to the high possibility of change induced by in vitro platelet activation. Therefore, there has been desire for the appearance of a more sensitive and specific platelet activation marker.

The detection of P-selectin as a platelet activation marker has been used in recent years (Shattil S. J. et al., *Blood*, Volume 70 (1987), pp. 307-315; Murakami T. et al., *Eur. J. Clin. Invest.*, Volume 26 (1996), pp. 996-1003). P-selectin is a membrane protein existing in the α-granule membrane of platelets and in the Weibel-Palade bodies of vascular endothelial cells; it migrates to the cell surface when these cells are suffered from a stimulus. P-selectin is currently categorized into two types, a membrane bound type and a soluble type. Membrane-bound P-selectin is directly detected using a fluorescence-labeled anti-P-selectin antibody and flow cytometry. However, sample handling can cause a pseudo-positive result for the expression of P-selectin in platelets, making it difficult to obtain consistent results. Soluble P-selectin, on the other hand, can be detected by sandwich ELISA. However, because P-selectin originates in platelets and vascular endothelial cells, the problem of its origin arises when the soluble P-selectin in plasma is measured.

Microscopic membrane vesicles are formed when platelets undergo activation under a variety of circumstances or are suffered from a physical stimulus; these membrane vesicles are called microparticles. Platelet microparticles are generally measured by flow cytometry, and this is important for comprehending the pathological condition of various thrombotic diseases. However, a number of problems have been noted here, such as (1) differences in sensitivity between instruments, (2) how the microparticle region is gated, (3) the fact that detection limit is near the size of the microparticles, and (4) differences between facilities based on the antibody used, and standardization of the measurement method has not been achieved.

The glycoprotein VI (GPVI) present on the platelet membrane is a collagen receptor of platelets, and it has been shown to have a central role in collagen-induced platelet activation (refer to Takayama H. *Japanese Journal of Thrombosis and Hemostasis*, Volume 14 (2003), Number 2, pp. 75-81). In addition, anti-mouse GPVI antibody has been reported to exhibit an antithrombotic activity by specifically inhibiting collagen-induced platelet aggregation without remarkable prolongation of bleeding time (refer to Nieswandt B. et al., *J. Exp. Med.*, Volume 194 (2001), Number 4, pp. 459-469). It has also been reported that anti-human GPVI antibody exhibits an antithrombotic activity without causing a remarkable prolongation of bleeding time (Takayama H. et al., *Blood*, Volume 106 (2005), Number 11, p. 612a; WO 2005/111083 A2). Accordingly, there is an expectation that a drug that specifically inhibits collagen-mediated platelet aggregation, for example, an anti-GPVI antibody, could be a safe and highly effective antiplatelet drug.

It has been reported that the GPVI present on platelets can be detected by western blotting (Tsuji M. et al., *J. Biol. Chem.*, Volume 272 (1997), Number 38, pp. 23528-23531). In addition, it has been confirmed by western blotting that shedding of GPVI occurs when anti-GPVI antibody is added to platelets and that soluble GPVI (sGPVI) appears in the culture supernatant (Bergmeier W. et al., *Thromb. Haemost.*, Volume 91 (2004), pp. 951-958). It has been suggested that this shedding of sGPVI is due to the action of a metalloprotease. However, this phenomenon was artificially induced ex vivo under conditions that can almost never occur physiologically, and it was completely unclear as to whether the shedding of platelet GPVI is actually occurred in vivo, under physiological or pathological conditions. Moreover, the detection of platelet GPVI and sGPVI by western blotting is itself encumbered by a number of problems with regard to its generalization into the clinical setting, such as preparation of the sample for testing and detection sensitivity. Furthermore, the number of GPVI expressed on the platelet surface is presumed to be extremely small at approximately 3000 per platelet. Thus, in order to diagnose thrombosis/embolism, the development of a simpler test method that exhibits a high specificity and a high detection sensitivity is desired.

DISCLOSURE OF THE INVENTION

Thus, with respect to the diagnosis of diseases associated with platelet activation/vascular endothelial injury, for example thrombosis, and selecting antiplatelet drug responders, there is desire for a highly reliable biomarker for platelet activation, a simple and highly sensitive method of determining the biomarker or method of diagnosis that yields consistent results, and a reagent or kit for them.

An object of the present invention is to provide a novel platelet activation marker and a reagent and method for its determination, and is to provide novel applications of the marker in, for example, the diagnosis of diseases associated with platelet activation/vascular endothelial injury.

In order to solve the problems cited above, the present inventors conceived of the idea that a convenient, high-sensitivity measurement of sGPVI present in plasma could be accessed by establishing a plurality of mouse hybridomas that produce antibody against GPVI and using a combination of the antibodies produced therefrom. As a result of extensive and intensive investigations based on this idea, the present inventors succeeded in establishing a specific and highly sensitive method of determining GPVI present on the platelet membrane (in some cases referred to as mGPVI in the following) and soluble GPVI present in body fluids (in some cases referred to as sGPVI in the following) and discovered that this can be a platelet activation marker, and accomplished the present invention.

The present invention is described in the following.

The first embodiment of the present invention is (1) a method of determining GPVI in a sample, particularly sGPVI or mGPVI in a biological sample, using at least one substance that specifically binds GPVI; and preferably is (1a) a method of determining soluble GPVI (sGPVI) in a body fluid, particularly a human body fluid, using at least one substance that specifically binds GPVI;

(1b) any of the preceding methods of determination, wherein the determination sensitivity is 100 pg/mL or less, preferably 30 pg/mL or less, more preferably 10 pg/mL or less, even more preferably 3.0 pg/mL or less, particularly preferably 1.0 pg/mL or less;

(1-1) any of the preceding methods of determination, wherein the substance that specifically binds GPVI is an anti-GPVI antibody;

(1-1a) any of the preceding methods of determination, wherein the substance that specifically binds GPVI is an antibody that specifically binds to domain 1, preferably to loop 2 or loop 5 and more preferably to loop 2 of GPVI;

(1-1b) any of the preceding methods of determination, wherein the substance that specifically binds GPVI is an antibody that specifically binds to domain 2, preferably to loop 9 or loop 11 and more preferably to loop 9 of GPVI;

(1-1c) any of the preceding methods of determination, wherein the substance that specifically binds GPVI is an antibody that specifically binds to loop 2 or loop 9 of GPVI;

(1-2) any of the preceding methods of determination, wherein at least two anti-GPVI antibodies having different binding sites are used as the substance that specifically binds GPVI;

(1-3) any of the preceding methods of determination, wherein at least an anti-GPVI antibody that specifically binds to domain 1 of GPVI and/or an anti-GPVI antibody that specifically binds to domain 2 is (are) used as the substance that specifically binds GPVI;

(1-3a) any of the preceding methods of determination, wherein said anti-GPVI antibody that specifically binds to domain 1 of GPVI is an antibody that specifically binds to loop 2 or loop 5, preferably loop 2 of GPVI;

(1-3b) any of the preceding methods of determination, wherein said anti-GPVI antibody that specifically binds to domain 2 of GPVI is an antibody that specifically binds to loop 9 or loop 11 and preferably loop 9 of GPVI;

(1-3c) any of the preceding methods of determination, wherein said anti-GPVI antibody that specifically binds to domain 1 of GPVI is an antibody that specifically binds to loop 2 or loop 5 and preferably loop 2 of GPVI and said anti-GPVI antibody that specifically binds to domain 2 of GPVI is an antibody that specifically binds to loop 9 or loop 11 and preferably loop 9 of GPVI;

(1-4) any of the preceding methods of determination, wherein at least an antibody that specifically binds to loop 2 of GPVI and/or an antibody that specifically binds to loop 9 is (are) used as the substance that specifically binds GPVI;

(1-4a) any of the preceding methods of determination, wherein at least the antibody that specifically binds to loop 2 of GPVI is used in the form of a non-immobilized antibody;

(1-4b) any of the preceding methods of determination, wherein at least the anti-GPVI antibody that specifically binds to loop 9 of GPVI is used in the form of an immobilized antibody;

(1-4c) any of the preceding methods of determination, wherein at least the antibody that specifically binds to loop 2 of GPVI is used in the form of a non-immobilized antibody and the anti-GPVI antibody that specifically binds to loop 9 is used in the form of immobilized antibody;

(1-4d) any of the preceding methods of determination, that is a sandwich immunoassay method;

(1-4e) any of the preceding methods of determination, wherein the non-immobilized antibody is F(ab')2;

(1-4f) any of the preceding methods of determination, using a detection system with biotinylated non-immobilized antibody and poly-HRP-labeled streptavidin;

(1-4g) any of the preceding methods of determination, wherein said antibody that specifically binds to loop 2 of GPVI is F1232-10-2 antibody, or said antibody that specifically binds to loop 9 of GPVI is F1232-7-1 antibody;

(1-5) a method of determining sGPVI in a body fluid and particularly in a human body fluid, using at least an anti-GPVI antibody that specifically binds to domain 1 of GPVI and/or an anti-GPVI antibody that specifically binds to domain 2;

(1-5a) any of the preceding methods of determining sGPVI, wherein said anti-GPVI antibody that specifically binds to domain 1 of GPVI is an antibody that specifically binds to loop 2 or loop 5 of GPVI;

(1-5b) any of the preceding methods of determining sGPVI, wherein the anti-GPVI antibody that specifically binds to domain 2 of GPVI is an antibody that specifically binds to loop 9 or loop 11 of GPVI;

(1-5c) any of the preceding methods of determining sGPVI, wherein said anti-GPVI antibody that specifically binds to domain 1 of GPVI is an antibody that specifically binds to loop 2 or loop 5 of GPVI and said anti-GPVI antibody that specifically binds to domain 2 of GPVI is an antibody that specifically binds to loop 9 or loop 11 of GPVI;

(1-6) any of the preceding methods of determining sGPVI, using at least an anti-GPVI antibody that specifically binds to loop 2 of GPVI and/or an anti-GPVI antibody that specifically binds to loop 9;

(1-6a) any of the preceding methods of determining sGPVI, wherein at least the antibody that specifically binds to loop 2 of GPVI is used in the form of a non-immobilized antibody;

(1-6b) any of the preceding methods of determining sGPVI, wherein at least the anti-GPVI antibody that specifically binds to loop 9 of GPVI is used in the form of an immobilized antibody;

(1-6c) any of the preceding methods of determining sGPVI, wherein at least the antibody that specifically binds to loop 2 of GPVI is used in the form of a non-immobilized antibody and the anti-GPVI antibody that specifically binds to loop 9 is used in the form of an immobilized antibody;

(1-6d) any of the preceding methods of determination, that is a sandwich immunoassay method;

(1-6e) any of the preceding methods of determination, wherein the non-immobilized antibody is F(ab')2;

(1-6f) any of the preceding methods of determination, using a detection system using a biotinylated non-immobilized antibody and poly-HRP-labeled streptavidin; and (1-6g) any of the preceding methods of determination, wherein said antibody that specifically binds to loop 2 of GPVI is F1232-10-2 antibody and said antibody that specifically binds to loop 9 of GPVI is F1232-7-1 antibody.

The second embodiment of the present invention is (2) a reagent or kit for determining the GPVI in a sample, particularly the sGPVI or mGPVI in a biological sample, that comprises at least one substance that specifically binds GPVI; and preferably is (2a) a reagent or kit for determining the sGPVI in a body fluid and particularly in a human body fluid, that comprises at least one substance that specifically binds GPVI;

(2b) any of the preceding determination reagents or kits, wherein the determination sensitivity is 100 pg/mL or less, preferably 30 pg/mL or less, more preferably 10 pg/mL or less, even more preferably 3.0 pg/mL or less, and particularly preferably 1.0 pg/mL or less;

(2-1) any of the preceding determination reagents or kits, wherein the substance that specifically binds GPVI is an anti-GPVI antibody;

(2-1a) any of the preceding determination reagents or kits, wherein the substance that specifically binds GPVI is an antibody that specifically binds to domain 1 of GPVI, preferably loop 2 or loop 5 and more preferably loop 2 of GPVI;

(2-1b) any of the preceding determination reagents or kits, wherein the substance that specifically binds GPVI is an antibody that specifically binds to domain 2 of GPVI, preferably loop 9 or loop 11 and more preferably loop 9 of GPVI;

(2-1c) any of the preceding determination reagents or kits, wherein the substance that specifically binds GPVI is an antibody that specifically binds to loop 2 or loop 9 of GPVI;

(2-2) any of the preceding determination reagents or kits, which comprises at least two anti-GPVI antibodies having different binding sites as the substance that specifically binds GPVI;

(2-3) any of the preceding determination reagents or kits, which comprises an anti-GPVI antibody that specifically binds to domain 1 of GPVI and an anti-GPVI antibody that specifically binds to domain 2 as the substance that specifically binds GPVI;

(2-3a) any of the preceding determination reagents or kits, wherein said anti-GPVI antibody that specifically binds to domain 1 of GPVI is an antibody that specifically binds to loop 2 or loop 5, preferably loop 2 of GPVI;

(2-3b) any of the preceding determination reagents or kits, wherein said anti-GPVI antibody that specifically binds to domain 2 of GPVI is an antibody that specifically binds to loop 9 or loop 11, preferably loop 9 of GPVI;

(2-3c) any of the preceding determination reagents or kits, wherein said anti-GPVI antibody that specifically binds to domain 1 of GPVI is an antibody that specifically binds to loop 2 or loop 5, preferably loop 2 of GPVI and said anti-GPVI antibody that specifically binds to domain 2 of GPVI is an antibody that specifically binds to loop 9 or loop 11, preferably loop 9 of GPVI;

(2-4) any of the preceding determination reagents or kits, that comprises, as the substance that specifically binds GPVI, an antibody that specifically binds to loop 2 of GPVI and an anti-GPVI antibody that specifically binds to loop 9;

(2-4a) any of the preceding determination reagents or kits, that comprises at least the antibody that specifically binds to loop 2 of GPVI as a non-immobilized antibody;

(2-4b) any of the preceding determination reagents or kits, that comprises at least the anti-GPVI antibody that specifically binds to loop 9 of GPVI as an immobilized antibody;

(2-4c) any of the preceding determination reagents or kits, that comprises at least the antibody that specifically binds to loop 2 of GPVI as a non-immobilized antibody and the anti-GPVI antibody that specifically binds to loop 9 as an immobilized antibody;

(2-4d) any of the preceding determination reagents or kits, used in a sandwich immunoassay method;

(2-4e) any of the preceding determination reagents or kits, wherein the non-immobilized antibody is F(ab')2;

(2-4f) any of the preceding determination reagents or kits, that comprises biotinylated non-immobilized antibody and poly-HRP-labeled streptavidin;

(2-4g) any of the preceding determination reagents or kits, wherein said antibody that specifically binds to loop 2 of GPVI is F1232-10-2 antibody, or said antibody that specifically binds to loop 9 of GPVI is F1232-7-1 antibody;

(2-5) a reagent or kit for determining sGPVI in a body fluid and particularly in a human body fluid, that comprises at least an antibody that specifically binds to domain 1 of GPVI and/or an anti-GPVI antibody that specifically binds to domain 2;

(2-5a) any of the preceding reagents or kits for determining sGPVI, wherein said anti-GPVI antibody that specifically binds to domain 1 of GPVI is an antibody that specifically binds to loop 2 or loop 5 of GPVI;

(2-5b) any of the preceding reagents or kits for determining sGPVI, wherein the anti-GPVI antibody that specifically binds to domain 2 of GPVI is an antibody that specifically binds to loop 9 or loop 11 of GPVI;

(2-5c) any of the preceding reagents or kits for determining sGPVI, wherein said anti-GPVI antibody that specifically binds to domain 1 of GPVI is an antibody that specifically binds to loop 2 or loop 5 of GPVI and said anti-GPVI antibody that specifically binds to domain 2 of GPVI is an antibody that specifically binds to loop 9 or loop 11 of GPVI;

(2-6) any of the preceding reagents or kits for determining sGPVI, that comprises at least an antibody that specifically binds to loop 2 of GPVI and/or an anti-GPVI antibody that specifically binds to loop 9;

(2-6a) any of the preceding reagents or kits for determining sGPVI, that comprises at least the antibody that specifically binds to loop 2 of GPVI as a non-immobilized antibody;

(2-6b) any of the preceding reagents or kits for determining sGPVI, that comprises at least the anti-GPVI antibody that specifically binds to loop 9 of GPVI as an immobilized antibody;

(2-6c) any of the preceding reagents or kits for determining sGPVI, that comprises at least the antibody that specifically binds to loop 2 of GPVI as a non-immobilized antibody and the anti-GPVI antibody that specifically binds to loop 9 as an immobilized antibody;

(2-6d) any of the preceding determination reagents or kits, that is used in a sandwich immunoassay method;

(2-6e) any of the preceding determination reagents or kits, wherein the non-immobilized antibody is F(ab')2;

(2-6f) any of the preceding determination reagents or kits, that comprises biotinylated non-immobilized antibody and poly-HRP-labeled streptavidin; and (2-6g) any of the preceding determination reagents or kits, wherein said antibody that specifically binds to loop 2 of GPVI is F1232-10-2 antibody and said antibody that specifically binds to loop 9 of GPVI is F1232-7-1 antibody.

The third embodiment of the present invention is (3) a platelet activation marker comprising sGPVI or mGPVI.

The fourth embodiment of the present invention is (4) use of sGPVI or mGPVI as a platelet activation marker.

The fifth embodiment of the present invention is (5) a method of detecting, determining, quantitating, assessing, or evaluating platelet activation or vascular endothelial injury, comprising:

detecting, determining, or quantitating the sGPVI or mGPVI in a sample; and (5-1) a method of detecting, determining, quantitating, assessing, or evaluating platelet activation or vascular endothelial injury, comprising:

detecting, determining, or quantitating GPVI, particularly sGPVI, more preferably sGPVI in a human body fluid, using any of the preceding methods or reagents or kits for determining GPVI, particularly sGPVI.

The sixth embodiment of the present invention is (6) a method of diagnosing a disease associated with platelet activation or vascular endothelial injury, a method of assessing the susceptibility to a disease associated with platelet activation or vascular endothelial injury, or a method of evaluating the risk of developing a disease associated with platelet activation or vascular endothelial injury, comprising:

detecting, determining, or quantitating sGPVI or mGPVI in a sample;

(6-1) the aforementioned method of diagnosing a disease associated with platelet activation or vascular endothelial injury, method of assessing the susceptibility to a disease associated with platelet activation or vascular endothelial injury, or method of evaluating the risk of developing a disease associated with platelet activation or vascular endothelial injury, comprising:

detecting, determining, or quantitating the GPVI, particularly the sGPVI, more preferably the sGPVI in a human body fluid, using any of the preceding methods or reagents or kits for determining GPVI, particularly sGPVI; and (6-2) any of the aforementioned methods of diagnosis, susceptibility assessment, or risk evaluation, wherein said disease is preferably a thrombotic disease or an embolic disease or an arteriosclerotic disease, more preferably is any selected from the group consisting of angina pectoris, myocardial infarction, heart disease, cerebral infarction, and dementia.

The seventh embodiment of the present invention is (7) a method of selecting patients who respond or respond well to an antiplatelet drug, preferably an antiplatelet drug that inhibits collagen-induced platelet activation or aggregation, and more preferably an anti-GPVI antibody, comprising:

detecting, determining, or quantitating sGPVI or mGPVI in a sample;

(7-1) the aforementioned method of selecting patients who respond an antiplatelet drug, preferably an antiplatelet drug that inhibits collagen-induced platelet activation or aggregation, more preferably an anti-GPVI antibody or GPVI-Fc, comprising:

detecting, determining, or quantitating GPVI, particularly sGPVI in a sample, more preferably sGPVI in a human body fluid, using any of the preceding methods or reagents or kits for determining GPVI and particularly sGPVI; and (7-2) any of the aforementioned selecting methods, wherein the disease suspected to affect the patient is a disease associated with platelet activation or vascular endothelial injury, preferably is a thrombotic disease or an embolic disease or an arteriosclerotic disease, more preferably is any selected from the group consisting of angina pectoris, myocardial infarction, heart disease, cerebral infarction, and dementia.

The eighth embodiment of the present invention is (8) a method of deciding the time for the (beginning of) administration of an antiplatelet drug and preferably an antiplatelet drug that inhibits collagen-induced platelet activation or aggregation, comprising:

detecting, determining, or quantitating sGPVI or mGPVI in a sample;

(8-1) the aforementioned method of determination, comprising:

detecting, determining, or quantitating GPVI, particularly sGPVI, more preferably the sGPVI in a human body fluid, using any of the preceding methods or reagents or kits for determining GPVI, particularly sGPVI, more preferably sGPVI in a human body fluid; and (8-2) any of the aforementioned methods of determination, wherein the disease suspected to affect the patient receiving said drug is a disease associated with platelet activation or vascular endothelial injury, preferably is a thrombotic disease or an embolic disease or an arteriosclerotic disease, and more preferably is any selected from the group consisting of angina pectoris, myocardial infarction, heart disease, cerebral infarction, and dementia.

The ninth embodiment of the present invention is (9) a method of predicting, or a method of monitoring, or a method of prognostically assessing the therapeutic effects of, or the occurrence of side effects by, an antiplatelet drug, preferably an antiplatelet drug that inhibits collagen-induced platelet activation or aggregation, comprising:

detecting, determining, or quantitating sGPVI or mGPVI in a sample; (9-1) the aforementioned method of predicting, monitoring, or prognostically assessing, comprising:

detecting, determining, or quantitating sGPVI in a human body fluid using the aforementioned methods, reagents, or kits for determining sGPVI in a human body fluid; and (9-2) any of the aforementioned methods of predicting, monitoring, or prognostically assessing, wherein said disease suspected to affect the patient is a disease associated with platelet activation or vascular endothelial injury, preferably is a thrombotic disease or an embolic disease or an arteriosclerotic disease, more preferably is any selected from the group consisting of angina pectoris, myocardial infarction, heart disease, cerebral infarction, and dementia.

The tenth embodiment of the present invention is

(10) a reagent or kit for any of the methods in the preceding fifth to ninth embodiments of the present invention, that comprises at least one substance that specifically binds GPVI.

The eleventh embodiment of the present invention is

(11) a method of preventing or treating a disease, comprising:

administering an antiplatelet drug, preferably an antiplatelet drug that inhibits collagen-induced platelet activation or aggregation, to a patient who has been diagnosed or selected by the diagnostic method or selecting method as described above;

(11-1) a method of preventing or treating a disease, comprising:

administering anti-GPVI antibody or GPVI-Fc, preferably anti-GPVI antibody to a patient who has been diagnosed or selected by the diagnostic method or selecting method as described above; and (11-2) any of the aforementioned methods of preventing or treating a disease, wherein said disease is a disease associated with platelet activation or vascular endothelial injury, preferably is a thrombotic disease or an embolic disease or an arteriosclerotic disease, more preferably is any selected from angina pectoris, myocardial infarction, heart disease, cerebral infarction, and dementia.

The twelfth embodiment of the present invention is

(12) a drug for preventing or treating a disease in a patient who has been diagnosed or selected by the diagnostic method or selecting method as described above, wherein said drug comprises an antiplatelet drug, preferably comprises an antiplatelet drug that inhibits collagen-induced platelet activation or aggregation;

(12-1) a drug for preventing or treating a disease in a patient who has been diagnosed or selected by the diagnostic method or selecting method as described above, wherein the drug comprises anti-GPVI antibody or GPVI-Fc, preferably anti-GPVI antibody; and (12-2) any of the aforementioned drugs, wherein said disease is a disease associated with platelet activation or vascular endothelial injury, preferably is a thrombotic disease or an embolic disease or an arteriosclerotic disease, more preferably is any selected from the group consisting of angina pectoris, myocardial infarction, heart disease, cerebral infarction, and dementia.

GPVI in a sample and particularly sGPVI or mGPVI in a biological sample can be determined at a high sensitivity by a determination method, a determination reagent, or a kit according to the present invention.

Moreover, the detection, determination, or quantitation of sGPVI or mGPVI using a determination method, a determination reagent, or a kit according to the present invention makes it possible, inter alia, to detect, determine, quantitate, assess, or evaluate platelet activation or vascular endothelial injury; to diagnose a disease associated with platelet activation or vascular endothelial injury, or assess the susceptibility to such a disease or evaluate the risk of developing such a disease; to select patients who respond to antiplatelet drugs and particularly anti-GPVI antibody; to decide the time for the (beginning of) administration of such drugs; and to predict, monitor, or prognostically assess the therapeutic efficacy of such drugs or their occurrence of side effects.

BRIEF DESCRIPTION OF THE DRAWINGS

FIG. 1 shows the nucleic acid sequence of the rat GPVI gene;

FIG. 2 shows the alignment of the amino acid sequences of human and rat GPVI and the positions of the each domains and loops (L1 to L14);

FIG. 3 shows the alignment of the amino acid sequences of human and mouse GPVI and the positions of the each domains and loops (L1 to L14);

FIG. 17 shows experimental results using rat endotoxin-induced thrombosis model;

FIG. 22 shows the results of GPVI western analysis of human platelets.

BEST MODE FOR CARRYING OUT THE INVENTION

Figure 4:
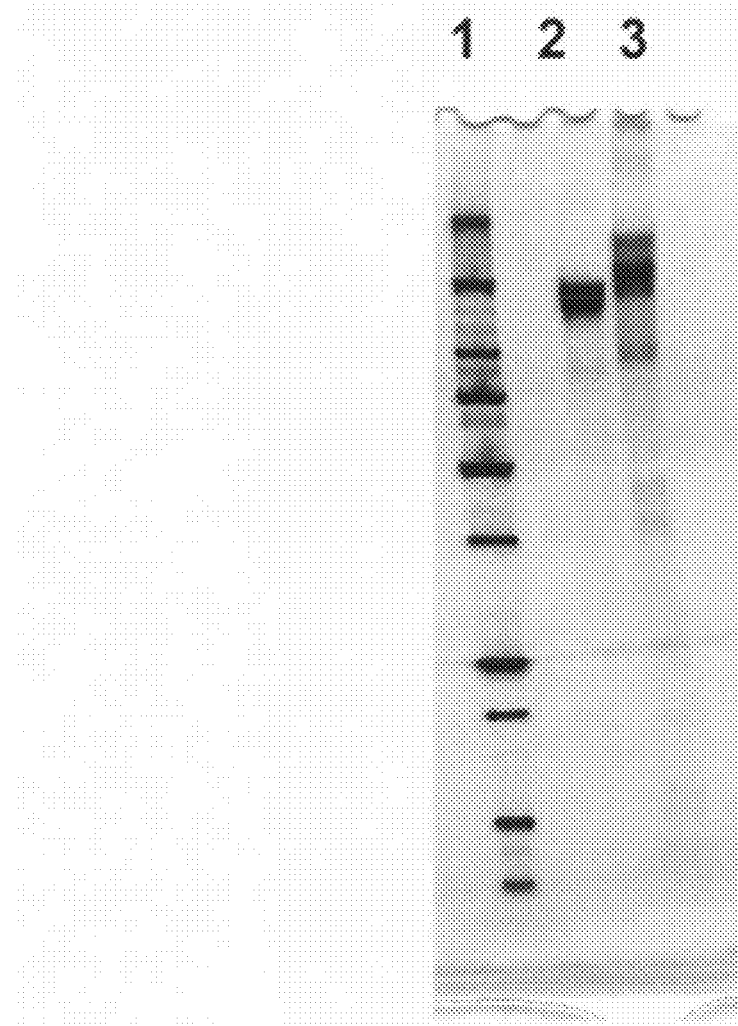
FIG. 4 shows the results from SDS-PAGE of recombinant rGPVI-Fc.

The present invention is described in detail in the following.

The animal species that is the source of GPVI for determination is not particularly limited and is a mammal, for example, mouse, rat, or monkey, wherein human GPVI is preferred. The nucleotide sequences and amino acid sequences of these GPVIs are known, and the amino acid sequences of mouse, rat, and human GPVI are shown in FIGS. 1 to 3. mGPVI is present as a transmembrane protein on the platelet surface; is generally a full-length GPVI molecule; and comprises an amino acid sequence as cited above. sGPVI has been released from the platelet due to some cause and is believed to be rendered soluble by enzymatic cleavage, particularly by an enzyme, preferably a protease and more preferably a metalloprotease derived from platelets. As shown in the examples, its molecular weight is, for example, about 55 kd by SDS-PAGE under a reducing condition, and it can be detected by, for example, western blotting using an anti-GPVI antibody.

The samples (in some cases referred to below as the specimen) in the present invention, particularly the biological samples are not necessarily limited and include body fluids, cells, and tissues. The body fluid can be exemplified by blood, plasma, platelet-rich plasma (PRP), platelet-poor plasma (PPP), urine, and so forth, while the cells can be exemplified by platelets. In the case of mGPVI, a platelet-containing biological sample is preferred, particularly blood, platelet-rich plasma (PRP), and platelets. In the case of sGPVI, a body fluid is preferred, particularly blood, plasma, platelet-poor plasma (PPP), urine, and so forth. The source animal species for the biological sample is also not necessarily limited and comprises mammals, for example, human, mouse, rat, rabbit, and so forth, wherein human is preferred.

The method of determining GPVI in a sample in accordance with the first embodiment of the present invention characteristically comprises determining GPVI in a sample, particularly sGPVI or mGPVI in a biological sample, using at least one substance that specifically binds GPVI. The reagent or kit for determining GPVI in a sample in accordance with the second embodiment of the present invention characteristically comprises at least one substance that specifically binds GPVI. The substance that specifically binds GPVI in the present invention encompasses collagen, CRP, convulxin, and so forth, and is preferably an anti-GPVI antibody. Antibodies are described in the following as a representative example; however, non-antibody substances that specifically bind GPVI can be based on the antibody-related description within the applicable range.

The anti-GPVI antibody is an antibody that specifically recognizes or binds GPVI, particularly sGPVI or mGPVI, but is not otherwise necessarily limited. The binding affinity (Kd) with GPVI is no greater than $10^{-7}$ M, preferably no greater than $3 \times 10^{-8}$ M, more preferably no greater than $1 \times 10^{-8}$ M, even more preferably no greater than $3 \times 10^{-9}$ M, and particularly preferably no greater than $1 \times 10^{-9}$ M.

The animal source species for the antibody is not necessarily limited and can be, for example, a mammal and particularly the mouse, rat, hamster, rabbit, and so forth; moreover, the antibody can also be produced by gene recombination techniques. Monoclonal antibody or polyclonal antibody can be used, wherein monoclonal antibody is preferred from the standpoints of physical uniformity and properties such as the specificity.

The form of the antibody in the present invention is not necessarily limited, and various form can be employed. For example, the antibody in the present invention may—as long as its activity (e.g., capacity to bind GPVI) is present—be a fragment, portion, or derivative of an antibody. The fragment can be, for example, Fab (fragment antigen binding), Fab', (Fab')$_2$, and so forth, while the derivative can be, for example, a single-chain antibody (scFv), disulfide-stabilized antibody (dsFv), diabody, sc(Fv)$_2$, (refer, for example, to Orita T., *Blood,* 2005; 105:562-566), nanobody (refer, for example, to Cortez-Retamozo V., *Cancer Research* 64, 2853-2857, 2004), CDR-comprising peptide, and so forth. These can be produced by known methods.

It can be a known anti-GPVI antibody, for example, mouse anti-human GPVI monoclonal antibody (refer, inter alia, to WO 01/810, WO 02/80968, and WO 2005/111083), rat anti-mouse GPVI monoclonal antibody (Nieswandt et al.), rat anti-human GPVI monoclonal antibody hGP5C4 (refer to WO 2005/54294 and so forth), human single-chain antibody (scFv) (refer to WO 01/810, WO 03/54020, and so forth), and human anti-human GPVI monoclonal antibody (WO 05/7800).

An antibody having an identified binding region, binding site, or epitope is preferred, for example, an antibody that binds with a specific domain, for example, domain 1 or domain 2, or an antibody that recognizes a particular loop, for example, at least a portion of loop 2 or loop 9. Specific examples are the antibodies provided in the examples herein and the antibodies described in the examples of WO 2006/117910 and WO 2006/118350. Various methods can be used to produce and identify such antibodies, and, while the known methods can also be applied, a preferred method uses, as its immunizing antigen or antigen for antibody identification, mutants in which a specific site on GPVI, for example, a specific domain, preferably a specific loop region, has been substituted by another amino acid sequence, specifically by the corresponding amino acid sequence from GPVI of another animal species. In specific terms, the methods described in this application or the methods described in the examples of WO 2006/117910 or WO 2006/118350 can be used. In addition, the recognition sites and so forth of these antibodies can be estimated by measurement, in accordance with known methods, of the binding capacity between the said substitution mutants and the antibody and the binding capacity between GPVI and the antibody. Specific methods are given in the examples.

A highly specific, highly selective, and/or highly sensitive detection or determination of GPVI is made possible by the use of one or two or more of these antibodies in which, for example, the binding site has been identified, preferably by the use of two species that have different, for example, binding sites, preferably by the use of a combination of antibodies that do not compete with one another in their binding with GPVI, for example: the combination of an antibody that binds to domain 1 with an antibody that binds to domain 2, or the combination of an antibody that binds to at least a portion of loop 2 with an antibody that binds to at least a portion of loop 9. When, in particular, a plurality of GPVI molecular species are present as a mixture, a specific GPVI molecular species therein, for example, sGPVI, can thereby be determined specifically, selectively, and/or sensitively. Suitable examples are shown in the examples hereinbelow.

The determination sensitivity in the present invention is not necessarily limited, and, expressed as the concentration in the sample, is 1 ng/mL or less, preferably 300 pg/mL or less, more preferably 100 pg/mL or less, even more preferably 30 pg/mL or less, particularly preferably 10 pg/mL or less, very preferably 3.0 pg/mL or less, and most preferably 1.0 pg/mL or less. In addition, the detection limit concentration is 1 ng/mL or less, preferably 300 pg/mL or less, more preferably 100 pg/mL or less, even more preferably 30 pg/mL or less, particularly preferably 10 pg/mL or less, very preferably 3.0 pg/mL or less, and most preferably 1.0 pg/mL or less. That is, with respect to the detection limit concentration, this is 1 ng/mL or less, preferably 300 pg/mL or less, more preferably 100 pg/mL or less, still more preferably 30 pg/mL or less, particularly preferably 10 pg/mL or less, very preferably 3.0 pg/mL or less, and most preferably 1.0 pg/mL or less. The concentration in the sample may be expressed in terms of the quantity of the standard material, for example, GPVI-Fc, used to construct the standard curve. In addition, when dilution of the sample is required prior to the determination, the concentration in the sample is the value post-dilution.

When soluble GPVI in a sample and particularly in plasma is to be determined, GPVI released from the platelet must be specifically determined free of influence from the plasma components. A sandwich immunoassay procedure using a highly specific enzyme is therefore generally employed. In order to accurately determine GPVI in the determination method of the present invention, it is important here to reduce the influence of the plasma components as much as possible, and dilution of the specimen is primarily selected as the means for doing this. While a component such as, for example, surfactant, can also be added to the reaction fluid for the purpose of reducing this influence, such components have the potential for influencing the determination system. Thus, in order to carry out an accurate determination of GPVI, the determination is preferably carried out with specimen dilution, and a high sensitivity is then required as a matter of necessity. Using the method provided in Example 8, sGPVI concentration in normal human plasma is in the range of approximately 0.1 to 10 ng/mL (median=0.4 ng/mL) as the quantity of hGPVI-hFc. In order to carry out an accurate determination on the specimen, the determination must be run with the specimen diluted in general at least 5-fold, preferably at least 10-fold, more preferably at least 50-fold, and even more preferably at least 100-fold. Due to this, the sensitivity of the determination system desirably is 30 pg/mL or less, preferably 10 pg/mL or less, and more preferably several pg/mL or less. When the method of the present invention is used, specifically the methods provided in the examples and particularly the method provided in Example 8, an absorbance difference of about 40 mAbs is obtained at 3 pg/mL standard substance, and it is thus possible to obtain a satisfactory sensitivity using the present invention.

The anti-GPVI antibody in the determination method, determination reagent, or kit according to the present invention may be a labeled antibody or may be an unlabeled antibody, but the use of at least one labeled antibody is preferred. The labeling substance and the labeling method employed for this labeling can be a known substance and a known method, and any of radioactive substances, enzymes, fluorescent substances, chemiluminescent substances, and so forth, can be used and applicable. Methods that use enzyme-labeled antibody are preferred among the preceding because they do not require special facilities or expensive detection instrumentation and because they also provide convenience in handling. Direct and indirect methods are available for labeling, and either of these can be used.

The determination principle and so forth in the determination method of the present invention is not necessarily limited, and is generally an immunoassay method and can be exemplified by known methods, for example, enzyme-antibody methods, ELISA methods, sandwich immunoassay methods, agglutination methods, solid-phase direct methods, solid-phase binding methods, solution reaction methods, competitive assays, non-competitive assays, immunochromatographic methods, and flow-through methods; a single one of these methods can be used or combinations can be used (refer, for example, to *Ultrasensitive Enzyme Immunoassay Methods*, Eiji ISHIKAWA, Japan Scientific Societies Press (1993); *New Uses of Immunoassay Methods and Their Applications to the Development of Diagnostic Reagents and Therapeutic Drugs*, Association for Research and Development in Immunoassay Methods, Keiei Kyoiku Publishing; and *Enzymatic Immunoassay Methods* (Third Edition), edited by Eiji ISHIKAWA et al., Igaku Shoin (1987)). The following can also be used: determination by the MEDIA method (Japanese Patent Application Laid-open No. H5-264552), which employs electrochemical determination of the signal from the label; immunoassays that employ a microchip (*Bioscience and Industry*, Volume 61 (2003), pp. 449-454); time-resolved immunofluorometric assays (*Analytical Biochemistry* (USA), Volume 137 (1984), pp. 335-343); and homogeneous immunoassay methods. Among the preceding, sandwich immunoassay methods—particularly sandwich ELISA methods that use an insoluble carrier, e.g., a microwell plate and so forth—are convenient and are also preferred from the standpoint of sensitivity.

The known technology can be employed for the sandwich immunoassay method. The principles and applications of this determination method and improvements thereto are described in, for example, *Ultrasensitive Enzyme Immunoassay Methods*, Eiji ISHIKAWA, Japan Scientific Societies Press (1993); *New Uses of Immunoassay Methods and Their Applications to the Development of Diagnostic Reagents and Therapeutic Drugs*, Association for Research and Development in Immunoassay Methods, Keiei Kyoiku Publishing; and *Enzymatic Immunoassay Methods* (Third Edition), edited by Eiji ISHIKAWA et al., Igaku Shoin (1987).

The sandwich immunoassay method generally is a method in which determination is carried out by the formation of an antibody-antigen-antibody complex using at least two antibody species that differ in their recognition sites for the protein being determined. Sandwich immunoassay methods generally employ an insoluble carrier, and in such a case the first antibody, which is bonded to the insoluble carrier, is referred to as the immobilized antibody or as the antibody for immobilization or as the capture antibody, while the second antibody is referred to as the non-immobilized antibody, the liquid-phase antibody, the detection antibody, or the labeled antibody when directly or indirectly labeled. An insoluble carrier having the first antibody bonded thereto is first prepared to give a solid-phase or reaction site. The specimen is added to this solid-phase insoluble carrier to carry out a reaction. After reaction for a prescribed period of time, washing is carried out to remove substances that have not specifically bound to the solid phase. The labeled second antibody is then added. After reaction for a prescribed period of time, washing is done to remove the labeled antibody that has not participated in complex formation, and, based on the label, the amount of complex specifically bound to the solid phase is specifically qualitated or quantitated. This sandwich method can be carried out by a procedure in which two steps are implemented as described above (a two-step method) or by a single step procedure in which the antigen and labeled antibody are added at the same time (one-step method).

Various antibodies can be used as the immobilized antibody in the present invention, but the immobilized antibody is, for example, preferably an antibody that specifically binds to domain 2, more preferably to loop 9 or loop 11, particularly to loop 9. While various antibodies can be used for the non-immobilized antibody, the non-immobilized antibody is, for example, preferably an antibody that specifically binds to domain 1, more preferably to loop 2 or loop 5, particularly to loop 2. Among those, preferred is the combination of the antibody that specifically binds to loop 9 for the immobilized antibody and the antibody that specifically binds to loop 2 for the non-immobilized antibody.

The sandwich immunoassay method can also be carried out in solution without using an insoluble carrier. An example here is a procedure in which antigen is reacted in the liquid phase with a labeled antibody and a second binding substance tagged with a second label and the interaction between the label and the second label is determined. In another approach, determination can also be carried out in the sandwich immunoassay method and so forth by a competitive method. This is a method in which determination is carried out based on the competition, during the formation of the antigen-antibody complex, between the antigen in the sample and a labeled antigen or a labeled antigen-like substance.

In yet another approach, determination can be carried out in the sandwich immunoassay method using a second specific binding. This is a method in which the determination is carried out by forming a complex comprising antibody-antigen-antibody-second specific binding substance or by forming a complex comprising antibody-antigen-antibody-second specific binding substance-specific binding partner for the second specific binding substance (in some cases referred to herebelow as the second specific binding partner). The second specific binding substance-second specific binding partner combination can be, inter alia, an antigen and its antibody, a ligand and its receptor, a sugar chain-containing substance and a lectin, and biotin and avidin or streptavidin. Additional examples are as follows: procedures that carry out determination using an antibody against an antibody, i.e., an anti-immunoglobulin antibody, to form an antibody-antigen-antibody-anti-immunoglobulin antibody complex, and procedures that carry out determination using an anti-immunoglobulin antibody and a second specific binding to form, inter alia, anti-immunoglobulin antibody-antibody-antigen-antibody-second specific binding substance-second specific binding partner.

As a preferred example of the present invention that employs two kinds of antibodies having different binding sites, a system is exemplified, in which using biotin and avidin or streptavidin as a second specific binding substance-second specific binding partner, one antibody, in particular the non-immobilized antibody is biotinylated and detected with a label, particularly with poly-HRP-labeled streptavidin. A specific example of this is provided in the examples.

The insoluble carrier used in the sandwich immunoassay system of the present invention may be a bead, latex particle, magnetic particle, plate, tube, membrane, and so forth. The material of the bead, plate, or tube can be, for example, polystyrene, nylon, glass, silicone rubber, stainless steel, plastic, and so forth. The membrane can be, for example, cellulose, a cellulose derivative, nitrocellulose, a porous synthetic polymer, glass fiber, a fabric, a nonwoven fabric, filter paper, and so forth. With regard to shape, a spherical shape can be used for the bead, latex particle, magnetic particle, and so forth. This is advantageous in terms of preserving space during storage. A well shape can be used for the plate and tube. This is advantageous in terms of being applicable to commercial automatic assay instrumentation, plate readers, and so forth. A membrane can also be used in immunochromatographic and flow-through methods. Bonding to the insoluble carrier of the antibody, second binding substance, second specific binding substance or its partner, or anti-immunoglobulin antibody can be effected by, for example, thermal adsorption, chemical bonding, and so forth.

In order to reduce reactions such as nonspecific adsorption and so forth and raise the specificity or sensitivity of the determination system, a blocking treatment with a substance that does not influence the determination system is preferably carried out on its non-adsorbing surfaces of the insoluble carrier, where the aforementioned substances are not bound. The following are examples of the substance that does not influence the determination system: proteins such as bovine serum albumin (BSA) and casein and surfactants such as Tween 20 and NP-40.

The label used in the sandwich immunoassay system kit of the present invention can be exemplified by enzymes such as peroxidase and particularly horseradish peroxidase (HRP), alkaline phosphatase, β-D-galactosidase, oxidase, uricase, and so forth; chemiluminescent substances such as acridinium and derivatives thereof, aequorin and variants thereof, and so forth; fluorescent substances e.g. FITC, lanthanoid, such as europium (Eu), samarium (Sm), and so forth; as well as dyes, colloidal gold, colored latexes, and isotopes.

3,3',5,5'-tetrabenzidine and 1,2-phenylenediamine are examples of the chromogenic substrate when a peroxidase is used as the enzyme; 4-nitrophenyl phosphate is an example of the chromogenic substrate when an alkaline phosphatase is used as the enzyme; and 2-nitrophenyl.β-D-galactoside is an example of the chromogenic substrate when β-D-galactosidase is used as the enzyme.

Labeling with the enzyme of the antibody, second binding substance, second specific binding substance or partner therefore, or anti-immunoglobulin antibody can be carried out by the two-step glutaraldehyde method, periodic acid method, maleimide method, pyridyl.disulfide method, and so forth. For non-enzyme labels, this can be done using the known art, e.g., thermal adsorption, chemical bonding, and so forth.

The use of an enzyme label with a chromogenic substrate as exemplified above makes it possible to carry out the determination using the usual absorbance measurement systems and also provides a relatively high sensitivity and for these reasons is preferred. The determination can be carried out by measurement instrumentation conforming to the particular label when a chemiluminescent substance, fluorescent substance, colored label, or isotope is used as the label. In addition, when a fluorescent substance such as Eu, for example, a cryptate ($Eu^{3+}$ cryptate), is used, the fluorescent resonance energy transfer can be determined using an allophycocyanine derivative, for example, XL665, as a second label. Dyes, colloidal gold, and colored lattices can also be visually evaluated and for this reason are preferred for the label used in easy-to-use determination kits, for example, kits that employ an immunochromatographic method or a flow-through method. The particles used as the insoluble carrier in an agglutination method can be those particles that are ordinarily used, for example, a latex, erythrocytes (for example, sheep erythrocytes), gelatin, microbeads, carbon particles, and so forth.

The determination reagent or kit of the present invention may contain optional constituent components or constituent elements in addition to the at least one substance that specifically binds GPVI. The optional constituent components in the determination reagent or kit can be exemplified by additives such as stabilizers, vehicles, preservatives, and so forth, while the optional constituent elements in the kit can be exemplified by diluents or buffer solutions for the standard substance, specimen, labeled antibody, and so forth, chromogenic substrate adapted to the enzyme when an enzyme is used in the labeled antibody, blocking agent, reaction stopper, rinsing agent, and so forth. While the diluent is not particularly limited, a diluent containing a substance present in the specimen is preferred. When the specimen is serum and the blood draw to acquire the serum has been carried out in the presence of EDTA or citric acid, the same amount of EDTA or citric acid is preferably also present in the diluent. For example, 0.2 to 1 mg/mL EDTA is preferably present in the diluent. The standard substance is, for example, GPVI, particularly sGPVI or mGPVI, prepared from a biological sample or recombinant GPVI, particularly sGPVI, mGPVI, the GPVI extracellular domain, or a fusion protein (GPVI-Fc) consisting of the GPVI extracellular domain and an immunoglobulin Fc fragment, prepared by genetic engineering. These can be prepared by known methods.

The determination reagent or kit of the present invention is particularly useful, for example, in the diagnostic methods described herebelow.

As shown in the examples below, because sGPVI and mGPVI exhibit variations—particularly a quantitative variation—accompanying the effects, inter alia, platelet activation induced by various in vivo and ex vivo platelet stimuli, they can be utilized as biomarkers, that is, platelet activation markers that estimate the status of platelet activation in vivo, particularly GPVI-mediated activation.

In specific terms, when, for example, sGPVI in a biological sample has a high value, it can be inferred that platelet activation has been induced in vivo due to some cause, particularly due to a GPVI-mediated mechanism. Moreover, when, for example, the platelet mGPVI has a high value, it can be inferred that a state exists in which the platelets are readily susceptible to activation with respect to platelet stimuli in vivo, particularly with respect to a GPVI-mediated stimulus. The cause, mechanism, or stimulus cited here can be exemplified by the exposure of vascular subendothelial collagen due to vascular endothelial injury.

That is, the present invention provides a platelet activation marker comprising soluble GPVI (sGPVI) or GPVI present on the platelet membrane (mGPVI) and further provides the use of sGPVI or mGPVI as a platelet activation marker.

Furthermore, diseases associated with platelet activation or vascular endothelial injury can, inter alia, be diagnosed based on the detection, determination, or quantitation of sGPVI or mGPVI. That is, the present invention provides a method of detecting, determining, quantitating, assessing, or evaluating platelet activation or vascular endothelial injury, comprising detecting, determining, or quantitating sGPVI or mGPVI in a sample (the fifth embodiment of the present invention);

a method of diagnosing, a method of assessing the susceptibility to, or a method of evaluating the risk of developing, a disease associated with platelet activation or vascular endothelial injury, comprising detecting, determining, or quantitating sGPVI or mGPVI in a sample (the sixth embodiment of the present invention);

a method of selecting for patients who respond to an antiplatelet drugs, preferably antiplatelet drugs that inhibit collagen-induced platelet activation or aggregation, more preferably an anti-GPVI antibody, comprising detecting, determining, or quantitating sGPVI or mGPVI in a sample (the seventh embodiment of the present invention);

a method of deciding the time for the (beginning of) administration of the aforementioned drug, comprising detecting, determining, or quantitating sGPVI or mGPVI in a sample (the eighth embodiment of the present invention);

a method of predicting, or a method of monitoring, or a method of prognostically assessing the therapeutic effects of, or the occurrence of side effects by, the aforementioned drug, comprising detecting, determining, or quantitating sGPVI or mGPVI in a sample (the ninth embodiment of the present invention); and a reagent or kit for any of the methods in the preceding fifth to ninth embodiments of the present invention, that comprises at least one substance that specifically binds GPVI (the tenth embodiment of the present invention).

The aforementioned methods of the fifth to ninth embodiments of the present invention comprise at least the detection, determination, or quantitation of sGPVI or mGPVI in a sample, particularly in a biological sample, and this comprises at least the step of bringing the sample into contact with at least one substance that specifically binds GPVI. The detection, determination, or quantitation of sGPVI or mGPVI in a sample can be carried out in accordance with the description of the first and second embodiments of the present invention, supra, using a determination method, determination reagent, or kit of the present invention.

When the sample is from a patient with a disease or from an individual at risk for a disease, a step can be included comprising comparison with the value determined for healthy individuals, or comparison of the value determined pre-onset with the value determined post-onset, or comparison of the value determined prior to treatment—and particularly treatment with a drug such as an antiplatelet drug—with the value determined after treatment. In an example of this step, the results of the determination in a plurality of normal individuals are obtained in advance; a standardized normal value or normal range, obtained by taking the average of these results or a range of these results, is made the standard normal value; and this is compared with the determined value. For example, the standard normal value may be acquired by designating the average value for normal individuals+2 SD or 3 SD as the cutoff value. In addition, a step may be implemented in which a reference value is established in advance for the patients of a disease, for example, a thrombotic disease, and this is compared with the determined value. This step may be carried out in place of the step of comparison with a standard normal value. The aforementioned methods of the fifth to ninth embodiments of the present invention can be effectively executed by carrying out these comparisons of the determination and/or the determined value.

The above-cited platelet activation is not necessarily limited in the present invention, but is preferably platelet activation due to a platelet agonist, more preferably is platelet activation due to a GPVI-specific agonist. Said platelet agonist can be exemplified by collagen, particularly the vascular subendothelial collagen associated with vascular endothelial injury, and otherwise by an anti-GPVI antibody that exhibits a platelet activation function, CRP, convulxin, and so forth.

For the purposes of the present invention, the diseases associated with platelet activation or vascular endothelial injury encompass abnormalities of the blood coagulation system and diseases that are caused by or associated with platelet activation or aggregation (particularly collagen-induced platelet activation or aggregation), vascular endothelial injury, and arteriosclerotic reactions, for example, diseases caused by or associated with up-regulation of the blood coagulation system. In particular, these are diseases caused by or associated with thrombus or embolus or arteriosclerosis, i.e., thrombotic or embolic diseases or arteriosclerotic diseases, for example, thrombosis, embolism, or arteriosclerosis. These diseases encompass not only arterial thrombosis, but also venous thrombosis and cerebral infarction caused by atrial fibrillation.

Specific examples are angina pectoris; myocardial infarction; and vascular endothelial hypertrophy, vessel restenosis, angina pectoris, and myocardial infarction during and after thrombolytic therapy, percutaneous transluminal coronary angioplasty, stent operation, bypass surgery, and artificial blood vessel operation. Additional examples are atrial fibrillation and atrial flutter and the thrombosis, embolism, particularly cerebral infarction caused thereby. Other examples are thromboangiitis obliterans, acute arterial occlusion, arteriosclerosis obliterans, deep venous thrombosis, and so forth, as well as cerebral infarction (atheromatous thrombotic infarction, lacunar infarction, cardiogenic infarction), transient cerebral ischemic attack, cerebrovascular spasm after subarachnoid bleeding, pulmonary thrombosis, pulmonary embolism, vascular purpura, idiopathic thrombocytopenic purpura, thrombotic thrombocytopenic purpura, disseminated intravascular coagulation syndrome, inhibition of blood coagulation during extracorporeal circulation (dialysis), systemic lupus erythematosus, multiple arteritis, antiphospholipid antibody syndrome, purpura nephritis, endothelial cell injury associated with diabetes mellitus, diabetic nephritis, diabetic retinopathy, nephritic embolism, complications associated with transplantation (hepatic veno-occlusive disease, graft-versus-host disease), and so forth. Thrombotic diseases, embolic diseases, and arteriosclerotic diseases (for example, thrombosis, embolism, and arteriosclerosis) are preferred, while angina pectoris, myocardial infarction, heart disease, cerebral infarction, and dementia are more preferred.

A determination of GPVI in a sample—particularly sGPVI or mGPVI in a biological sample—using the determination method, determination reagent, or kit of the present invention makes it possible to detect, determine, quantitate, assess, or evaluate platelet activation or vascular endothelial injury and also makes it possible to diagnose a disease associated with platelet activation or vascular endothelial injury, or to assess the susceptibility to such a disease, or to evaluate the risk of developing such a disease. The implementation of the preceding preferably is accompanied by a step of comparison with the value determined for healthy individuals, or comparison of the value determined pre-onset with the value determined post-onset, or comparison of the value determined prior to treatment—particularly treatment with a drug such as an antiplatelet drug—with the value determined after treatment.

The antiplatelet drug is not necessarily limited in the present invention and can be a known drug, for example, aspirin, ticlopidine, GPIIb/IIIa antagonist, and so forth. Various antiplatelet drugs can be used as the antiplatelet drug that specifically inhibits collagen-induced platelet activation or aggregation. Examples in this regard are antibodies against collagen; collagen peptide and fragments and derivatives thereof (refer, for example, to WO 99/50281 and so forth); and GPVI and fragments and derivatives thereof, for example, GPVI-Fc (refer, for example, to WO 01/810, WO 03/104282, and so forth). Anti-GPVI antibodies and GPVI-Fc are preferred, while anti-GPVI antibodies are more preferred. Known anti-GPVI antibodies can be used as this anti-GPVI antibody, for example, mouse anti-human GPVI monoclonal antibody (refer, inter alia, to WO 01/810, WO 02/80968, and WO 2005/111083), rat anti-mouse GPVI monoclonal antibody (Nieswandt et al.), rat anti-human GPVI monoclonal antibody hGP5C4 (refer to WO 2005/54294 and so forth), human single-chain antibody (scFv) (refer to WO 01/810, WO 03/54020, and so forth), and human anti-human GPVI monoclonal antibody (WO 05/7800). Preferred examples are antibodies that inhibit collagen-induced platelet aggregation, antibodies that exhibit a GPVI-depleting function, and antibodies that recognize loop 9 of GPVI. Specific examples here are the antibodies provided in the examples of this application and the antibodies described in the examples of WO 2006/117910 and WO 2006/118350.

The detection, determination, or quantitation of sGPVI or mGPVI in a sample in accordance with the determination method and so forth of the present invention makes it possible to screen for patients who respond to these drugs, to establish the (beginning) time for administration of these drugs, and to predict, monitor, or prognostically assess the therapeutic effects of these drugs or the occurrence of side effects by them. The implementation of the preceding is preferably accompanied by a step of comparison with a value determined in health individuals or comparison of the value determined prior to treatment—particularly treatment with a drug such as an antiplatelet drug—with the value determined after treatment.

With regard to the peripheral arterial occlusion associated with diabetes or the secondary prevention of myocardial infarction or cerebral infarction, the determination of soluble GPVI in the plasma and/or urine, selection of patients who exhibit high values, and administration to such patients of an anti-GPVI antibody or soluble GPVI-Fc, is predicted to provide a higher efficacy ratio than that without such patient selection. That is, the determination of the quantity of soluble GPVI in the blood and/or urine makes possible the selection of patients at high risk for thrombosis (e.g., myocardial infarction, cerebral infarction, peripheral arterial occlusion, and so forth) and also makes possible the selection of patients in whom an anti-GPVI antibody or soluble GPVI-Fc will be effective.

The amount of soluble GPVI in the plasma and/or urine may be determined after the execution of PCI. When the case of continuing antiplatelet therapy during the period in which the quantity of soluble GPVI presents high values is compared with the case of not continuing antiplatelet therapy, the rate of occurrence of cardiovascular events is predicted to be lower in the case in which continuation is carried out than in the case in which continuation is not carried out. That is, determination of the quantity of soluble GPVI in the plasma and/or urine enables an evaluation of the risk of the occurrence of thrombosis and enables a decision of the term for the administration of antiplatelet drugs.

EXAMPLES

The present invention is further described by the examples provided below; however, the present invention should not be understood as being limited by these examples.

Example 1

Cloning of the Rat GPVI Gene

First of all, primers (6 pairs) capable of amplifying each of the exons of the mouse GPVI gene were designed based on the known data of the mouse GPVI gene. With these primers, PCRs were carried out using rat genomic DNA as the template; the gene fragments that were specifically amplified were sequenced; and the nucleotide sequence of rat GPVI gene was estimated by connecting them. Next, based on this nucleotide sequence data, primers for rat GPVI (ratGPVI-#a, mGPVI-d) were redesigned, and the full-length rat GPVI gene was amplified by PCR using rat bone marrow cDNA (reverse transcripted from rat bone marrow RNA with oligo dT primer) as the template. The amplificated product was extracted from the gel and was cloned into TA-cloning vector pT7-Blue(T) (TAKARA BIO INC.), and its nucleotide sequence was determined. It was confirmed to be the same as the estimated sequence; this plasmid was named pTK-2478. The nucleotide sequence of the rat GPVI gene is shown in FIG. 1.

TABLE 1

| | | |
|---|---|---|
| exon 1 | rat GPVI-a | CCCTCAGCGCATCCTGTTCCTAT (SEQ ID NO: 1) |
| | rat GPVI-c | TTTCCCAGGTCACCTTCAGGACT (SEQ ID NO: 2) |
| exons 2, 3 | rat GPVI-f | TTAAGGGAGTCTCTAGCCTCTG (SEQ ID NO: 3) |
| | mGPVI-g | GTTTAGCATACACACCTGTAGCAATTAGCT (SEQ ID NO: 4) |
| exon 4 | rat GPVI-j | CCTGTTTCCTGTCTTTAATAGAG (SEQ ID NO: 5) |
| | rat GPVI-l | CCTTGCCCACACCTCTGACTCC (SEQ ID NO: 6) |
| exon 5 | rat GPVI-m | GTGAGAAAATCAAGTCACAGAAATG (SEQ ID NO: 7) |
| | rat GPVI-o | TTCAGACACATTTGTAGTAGAAC (SEQ ID NO: 8) |
| exon 6 | rat GPVI-r | GGAGCACTTGGGATGAACTGTCA (SEQ ID NO: 9) |
| | rat GPVI-s | GAGAAACCCATCCTCTTGCCAC (SEQ ID NO: 10) |
| exon 7 | rat GPVI-v | GCTTCACAAGCATATGAGCACGTG (SEQ ID NO: 11) |
| | rat GPVI-w | ATTATAGCTCTATAGATTCCATG (SEQ ID NO: 12) |
| full-length | rat GPVI-#a | GGGAATTCCATGTCTCCAGCCTCACTC (SEQ ID NO: 13) |
| | mGPVI-d | CCAAGTTATTTCTAGGCCAGTGG (SEQ ID NO: 14) |

Example 2

Construction of a Rat GPVI (D1D2) Mouse GPVI (D3)-Mouse Fc Fusion Protein (rGPVI-mFc) Expression Plasmid Using pTK-2478 as the template, a fragment 'A' encoding D1 and D2 of rat GPVI (extracellular domain 1 and domain 2 of GPVI) was amplified by PCR with the primer pair (rat GPVI-#a and rat GPVI-#t). Similarly, using pTK-2440 (described in WO 2006/117910 and WO 2006/118350) as the template, a fragment 'B' encoding D3 of mouse GPVI (region of extracellular domain of GPVI except D1 and D2) was amplified by PCR using the primer pair (rat GPVI-#s and IgG1-i). Then, using a mixture of 'A' and 'B' as the template, a fragment 'C', which was ligated rat GPVI (D1 and D2) and mouse GPVI (D3), was obtained by re-PCR using the primer pair (rat GPVI-#a and IgG1-i). After digestion of the 5' end of this fragment 'C' with Eco RI and the 3' end with Bam HI, the fragment 'C' was inserted into Eco RI and Bam HI sites of the plasmid (pTK-2299: described in WO 2006/117910 and WO 2006/118350) which comprises the mouse Fc region (mFc) at downstream from an EF promoter, then TK-2483, which was capable of expressing rat GPVI-mFc fusion protein, was constructed

TABLE 2

| | |
|---|---|
| IgG1-i | (SEQ ID NO: 15)<br>CCAGGAGTTCAGGTGCTGGGCACGGTGGGC |
| rat GPVI-#s | (SEQ ID NO: 16)<br>GTGGTTACTGGACCCTCTGCCACTCCCAGC |
| rat GPVI-#t | (SEQ ID NO: 17)<br>GCTGGGAGTGGCAGAGGGTCCAGTAACCAC |

The following expression plasmids were constructed by the same procedure as in Example 2, with reference to known methods (refer to, for example, WO 01/810, WO 03/54020, WO 2005/7800, and so forth) and based on the known human and mouse GPVI sequences, the rat GPVI sequence of FIG. 1, the alignment of human and rat GPVI amino acid sequences (FIG. 2), and the alignment of human and mouse GPVI amino acid sequences (FIG. 3): rat GPVI-hFc (rGPVI-hFc), in which the mFc has been substituted by the human Fc region (hFc); mouse GPVI-hFc (mGPVI-hFc); human GPVI-hFc (hGPVI-hFc); rGPVI-hL2,5-hFc (mutant GPVI protein in which loops 2 and 5 of rat GPVI-hFc have been replaced by the corresponding sequences of human GPVI); rGPVI-hL9,11-hFc (mutant GPVI protein in which loops 9 and 111 of rat GPVI-hFc have been replaced by the corresponding sequences of human GPVI); hGPVI-mL2-hFc (mutant GPVI protein in which loop 2 of human GPVI-hFc has been replaced by the corresponding sequence of mouse GPVI); and hGPVI-mL9-hFc (mutant GPVI protein in which loop 9 of human GPVI-hFc has been replaced by the corresponding sequence of mouse GPVI).

Example 3

Expression and Purification of rGPVI-mFc Fusion Protein

COS-1 cells were maintained in Dulbecco's MEM culture medium containing 10% fetal bovine serum. After mixing of the transfection reagent (FuGENE6, Roche Diagnostics) and serum-free Dulbecco's MEM culture medium, suitable amount of pTK-2483 was added and mixed, and this mixture was added to COS-1 cells that had been medium-exchanged to Hybridoma-SFM culture medium (Gibco). The supernatant was collected after cultivation for 3 days at 37° C./5% $CO_2$; cultivation was then carried out for an additional 3 days in fresh culture medium; and these supernatants were purified with a protein A column (Prosep-vA, Millipore) to yield antigen for use in the preparation of anti-rat GPVI antibody.

The obtained rGPVI-mFc fusion protein was subjected to SDS-PAGE analysis by an established method. In brief, the sample and molecular weight markers (Bio-Rad, Precision Plus Protein Unstained Standard) were applied to a 5 to 20% gradient gel followed by electrophoresis and silver staining (FIG. 4).

The following were also expressed and purified in the same manner: rGPVI-hFc fusion protein, mGPVI-hFc fusion protein, hGPVI-hFc fusion protein, rGPVI-hL2,5-hFc substituted mutant protein, rGPVI-hL9,11-hFc substituted mutant protein, and hGPVI-mL9-hFc substituted mutant protein.

Example 4

Preparation of Anti-Rat GPVI Monoclonal Antibody 12.5 μL alum (Pierce), 1 mg CpG adjuvant, and 20 μg purified rat GPVI-mFc fusion protein were mixed and 100 μL of antigen for administration was provided. Using a microsyringe, 50 μL of this antigen for administration was injected into each footpad on both feet of ddY mice (female, 8 weeks, SLC). After 11 days, 20 μg of the antigen for administration was diluted with 50 μL physiological saline and 25 μL of diluted antigen was administered into each of the footpads. After 3 days, lymphocytes were isolated from the iliac lymph nodes; the obtained lymphocytes were mixed with P3×63-Ag.8.U1 (ATTC) and cell fusion was then carried out using polyethylene glycol according to *Introduction to Monoclonal Antibody Experimental Procedures*, Tamie ANDO and Takeshi CHIBA (Kodansha). The hybridomas were selected using HAT culture medium, and after 1 weeks hybridomas producing the desired antibody were screened. In brief, purified rat GPVI-hFc fusion protein was diluted to 3 μg/mL with 0.076 M phosphate buffer solution (pH 7.4) (abbreviated below as PBS), and this solution was added to an immunoplate (Maxisorb, NUNC) at 50 μL/well. After reaction at 4° C. overnight, plate was washed three times with ion-exchanged water and then blocked by addition of 100 μL PBS containing 2% Stabilguard in each well. Culture supernatant was then added to each well, and plate was washed three times with physiological saline containing 0.05% Tween 20 after the incubation for 1 hour at 37° C. Peroxidase-labeled anti-mouse immunoglobulin antibody (Dako) was diluted 1000× with PBS containing 10% rabbit serum, and 50 μL of this solution was added to each well. After reaction for 1 hour at 37° C., plate was washed five times in the same manner and TMB solution (BioFix) was added to each well. After reaction for 10 minutes at room temperature, the reaction was stopped with 0.5 M sulfuric acid solution. The absorbance at 450 nm was measured with a plate spectrophotometer (NJ-2100, Nippon InterMed). Cells that had reacted with the purified rat GPVI-hFc fusion protein were selected and cloned by the limiting dilution method. After 11 days, 17 hybridoma clones producing the antibody that reacted with purified rat GPVI-hFc fusion protein were screened by same method (Table 3).

TABLE 3

| | | Immobilized antigen | |
|---|---|---|---|
| | Sample | Rat GPVI | Human GPVI |
| Sample | F1239-1-3 | 2.288 | 0.019 |
| | F1239-2-3 | 2.953 | 0.015 |
| | F1239-4-2 | 0.843 | 0.026 |
| | F1239-5-3 | 2.259 | 0.021 |
| | F1239-6-1 | 2.272 | 0.032 |
| | F1239-7-1 | 2.872 | 0.013 |
| | F1239-8-1 | 1.344 | 0.013 |

TABLE 3-continued

|  | Sample | Immobilized antigen | |
|---|---|---|---|
|  |  | Rat GPVI | Human GPVI |
|  | F1239-9-1 | 2.284 | 0.028 |
|  | F1239-10-2 | 2.061 | 0.021 |
|  | F1239-11-1 | 1.372 | 0.014 |
|  | F1239-15-3 | 1.552 | 0.023 |
|  | F1239-16-3 | 1.224 | 0.017 |
|  | F1239-17-2 | 1.502 | 0.014 |
|  | F1239-18-1 | 1.098 | 0.015 |
|  | F1239-19-1 | 2.93 | 0.017 |
|  | F1239-22-3 | 1.956 | 0.024 |
|  | F1239-23-1 | 2.668 | 0.021 |
| Control | Anti IgG | 2.944 | 2.84 |
|  | normal mouse IgG | 0.123 | 0.026 |
|  | F1232-37-2 | 0.137 | 2.757 |

Example 5

Production of Hybridoma-Produced Antibodies

Figure 5:
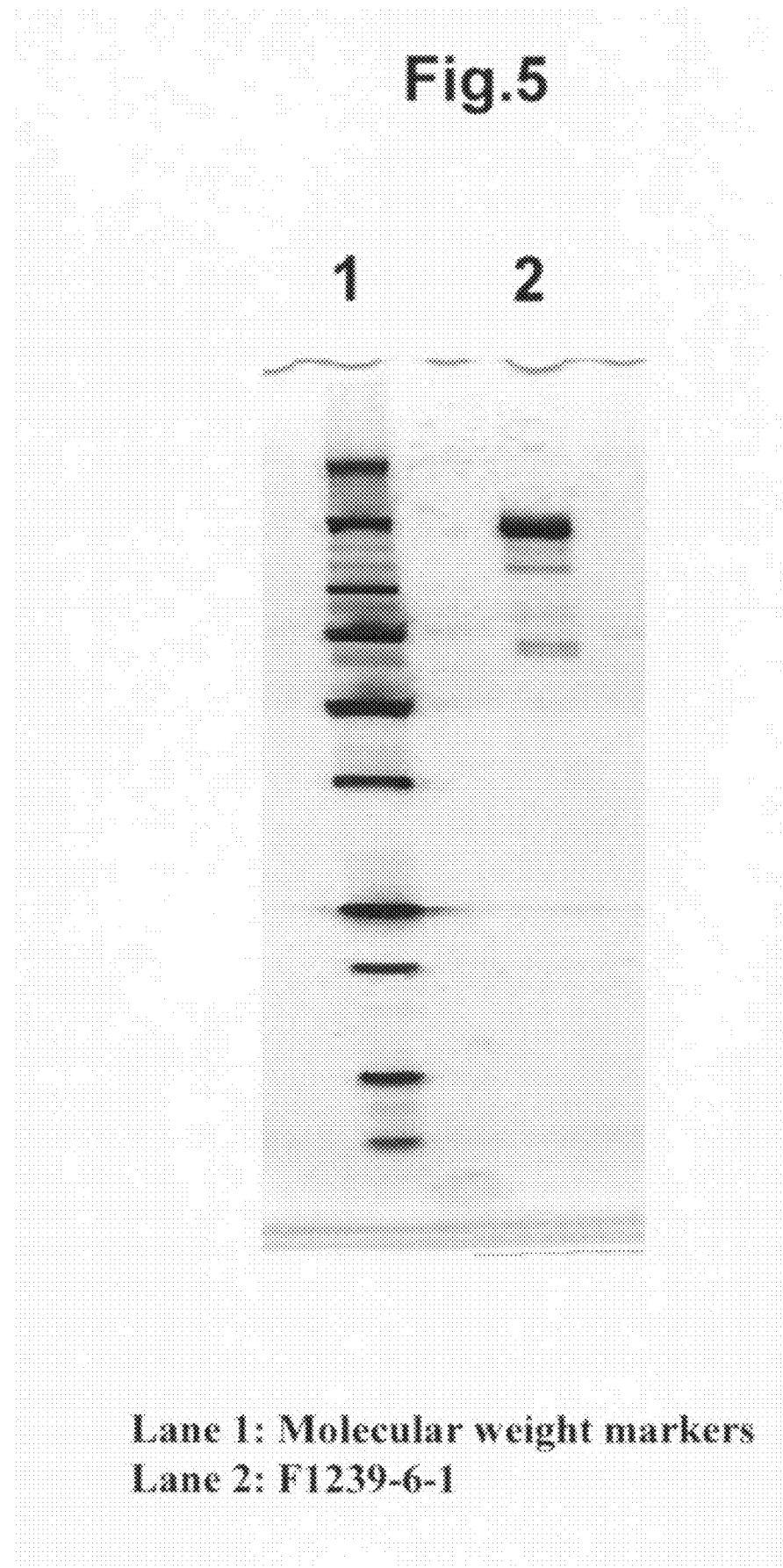
FIG. 5 shows the results from SDS-PAGE of F1239-6-1.

The following procedures were carried out at 4° C. unless stated otherwise. A culture supernatant was obtained by the clarification, at room temperature, of the mouse hybridoma culture fluid using a capsule cartridge filter having a pore diameter of 1 µm as a prefilter (Toyo Roshi Kaisha, Ltd. (Toyo Filter paper Ltd.)) and a Fluorodyne filter (Pall) having a pore diameter of 0.22 µm and a Millipak 200 (MILLIPORE) as the main filter, respectively. This culture supernatant was adsorbed on a protein A column (rmp Protein A Sepharose Fast Flow, GE Healthcare Biosciences) that had been preliminarily equilibrated with PBS (Sigma). After washing the unadsorbed protein with PBS, the non-specifically adsorbed protein was eluted with 10×PBS (Sigma). The protein A-bound antibody was subsequently eluted with 100 mM glycine-HCl buffer (pH 3.0). The volume of the eluate was measured and one-tenth volume of 2 M Tris-HCl (pH 8.5) was immediately added to return the pH to neutrality and a purified antibody solution was yielded. This purified antibody solution was concentrated with a Biomax PB ultrafiltration membrane (Millipore) having a molecular weight cut-off of 30,000 using a stirred cell, followed by dialysis against physiological saline (Otsuka Normal Saline, Otsuka Pharmaceutical Co., Ltd.), and finally obtained the purified antibody solution. The obtained antibody was analyzed with SDS-PAGE according to an established method. Thus, the sample and molecular weight markers (Bio-Rad, Precision Plus Protein Unstained Standard) were applied to a 5 to 20% gradient gel followed by electrophoresis and silver staining (FIG. 5). The antibodies used in the following all examples were purified by this same method.

Example 6

Recognition Regions of the Anti-Rat GPVI Antibodies

Figure 6:
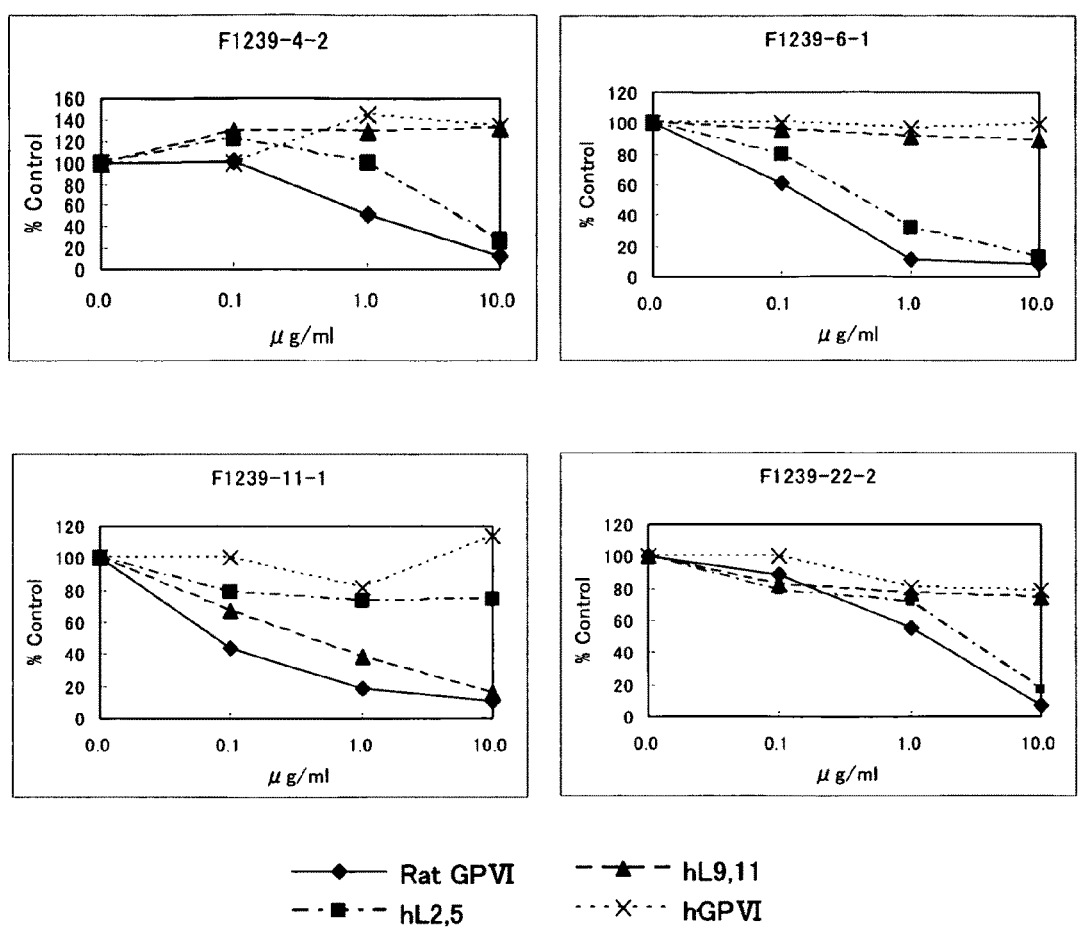
FIG. 6 shows the results of recognition region analysis of anti-rat GPVI antibodies.

The recognition domain of the anti-rat GPVI monoclonal antibodies obtained in Example 4 was analyzed. In brief, the purified rGPVI-hFc fusion protein was diluted to 2 µg/mL with PBS, and this solution was added to immunoplate (Maxisorb, NUNC) at 50 µL/well. After reaction for 1 hour at 37° C., plate was washed five times with ion-exchanged water and then blocked by addition of 100 µL PBS containing 2% Stabilgurd in each well. The monoclonal antibody, purified in Example 5, was then prepared in different concentrations and added to a polypropylene plate (NUNC) at 50 µL/well, and the rGPVI-hFc fusion protein, hGPVI-hFc fusion protein, rGPVI-hL2,5-hFc substituted mutant protein, or rGPVI-hL9,11-hFc substituted mutant protein obtained in Example 3 was added at 50 µL/well in each well with mixing. This mixed sample was added at 50 µL/well to the aforementioned immunoplate that immobilized with rGPVI-hFc fusion protein; after reaction for 1 hour at 37° C., plate was washed five times with physiological saline containing 0.05% Tween 20. Peroxidase-labeled anti-mouse kappa chain antibody (Rockland) was diluted to 1000× with PBS containing 10% rabbit serum and 50 µL of this solution was added to each well. After reaction for 1 hour at 37° C., plate was washed five times in the same manner, and TMB solution (BioFix) was added to each well. After reaction for 10 minutes at room temperature, the reaction was stopped with 0.5 M sulfuric acid solution. The absorbance at 450 nm was measured using a plate spectrophotometer (NJ-2100, Nippon InterMed). The results showed the presence of one antibody for which the absorbance was not reduced when rGPVI-hL2,5-hFc substituted mutant protein was added, that is, antibody that recognized loop 2 and/or loop 5 (F1239-11-1), and the presence of three antibodies for which the absorbance was not reduced when rGPVI-hL9,11-hFc substituted mutant protein was added, that is, antibody that recognized loop 9 and/or loop 11 (F1239-4-2, F1239-6-1, F1239-22-2) (FIG. 6). These three antibodies (F1239-4-2, F1239-6-1, F1239-22-2) did not react with mouse GPVI-hFc in this same method. Furthermore, when additionally considers that the amino acid sequence of loop 11 of rat GPVI is identical to the amino acid sequence of loop 11 of mouse GPVI, it is difficult to regard loop 11 as an important recognition region, and the aforementioned antibodies are presumed to recognize a structure that contains at least a portion of loop 9 of rat GPVI.

Example 7

Measurement of Rat Soluble GPVI by ELISA

Figure 7:
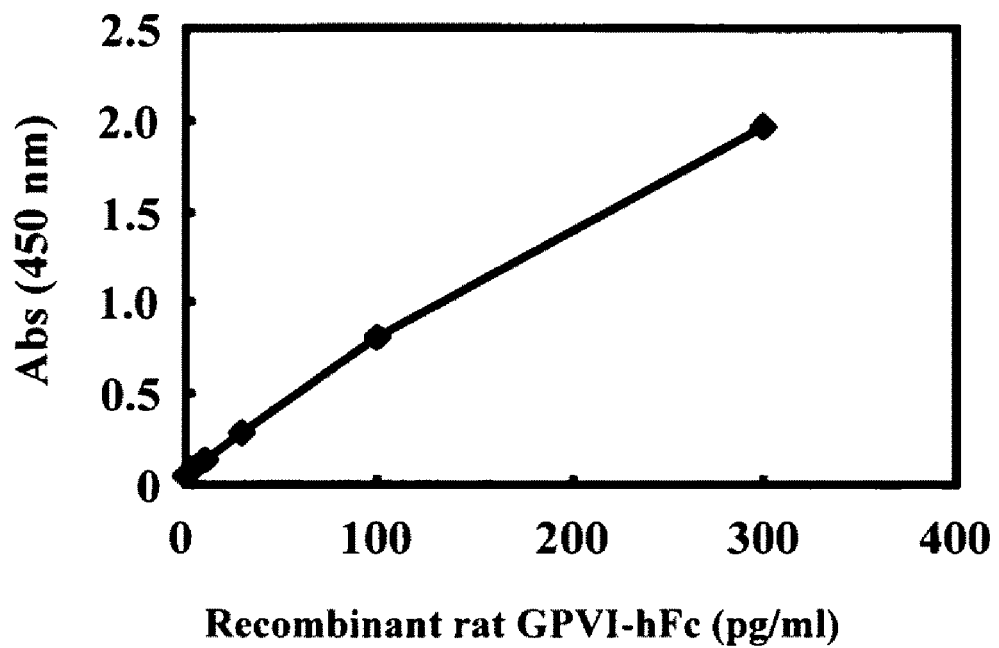
FIG. 7 shows the ELISA standard curve for rat soluble GPVI.

A sandwich ELISA system was constructed using the mouse anti-rat GPVI antibody prepared in Example 4. In brief, the purified F1239-6-1 antibody was diluted to 10 µg/µL with PBS, and this solution was added to immunoplate (Maxisorb, NUNC) at 75 µL/well. After reaction overnight at 4° C., plate was washed five times with ion-exchanged water and blocked by addition of 200 µL PBS containing 5% Stabilgurd and 0.1% Tween 20 in each well. The sample and recombinant rGPVI-hFc fusion protein, used as the standard, were diluted with 0.1% BSA, 0.3 M sodium chloride, 0.05% Tween 20/PBS. When plasma was used as the sample for determination, plasma was diluted to five times or more. Each sample was added at 50 µL/well. After reaction for 2 hours at 37° C. with stirring, plate was washed five times with physiological saline containing 0.05% Tween 20. Biotin-labeled F1239-7-1 F(ab')2 antibody was diluted with PBS containing 20% Poly-HRP DILUENT (Fitzgerald), 0.3 M sodium chloride and 0.05% Tween 20, and 50 µL of this solution was added to each well. After reaction for 1 hour at 37° C. with stirring, plate was washed five times in the same manner. Then, POLY-HRP80-Streptavidin (Fitzgerald) was diluted with PBS containing 20% Poly-HRP DILUENT and 0.05% Tween 20, and 50 µL of this solution was added to each well. After reaction for 30 minutes at 37° C. with stirring, plate was washed six times in the same manner, and TMB solution (BioFix) was added to each well. After reaction for 20 minutes at room temperature, the reaction was stopped with 0.5 M sulfuric acid solution. The absorbance at 450 nm was measured using a plate spectrophotometer (NJ-2100, Nippon InterMedic). FIG. 7 shows the standard curve using rGPVI-hFc fusion protein

Example 8

Measurement of Human Soluble GPVI by ELISA

Figure 8:
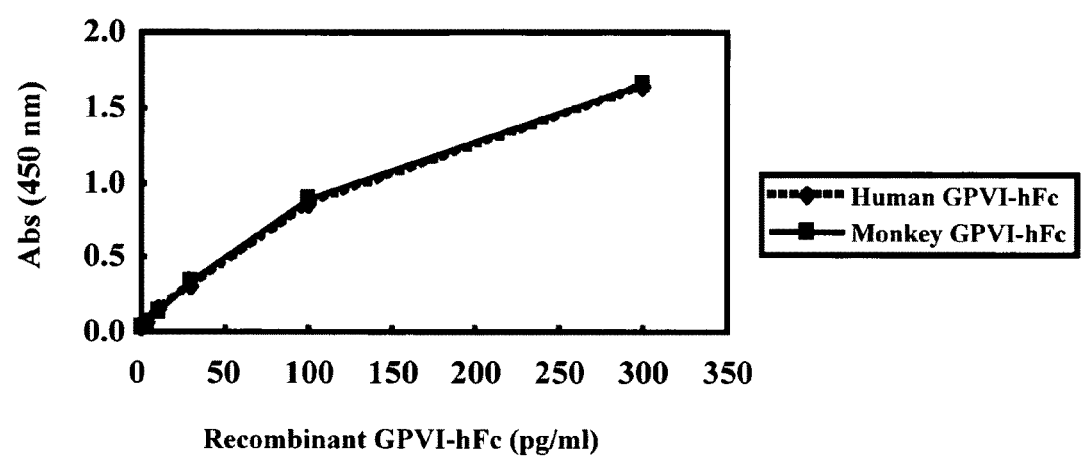
FIG. 8 shows the ELISA standard curve for human soluble GPVI.

A sandwich ELISA system was constructed using mouse anti-human GPVI antibody. In brief, the purified F1232-7-1 antibody was diluted to 10 μg/mL with PBS, and this solution was added to immunoplate (Maxisorb, NUNC) at 75 μL/well. After reaction overnight at 4° C., plate was washed five times with ion-exchanged water and blocked by addition of 200 μL PBS containing 5% Stabilgurd and 0.1% Tween 20 in each well. The sample and recombinant hGPVI-hFc fusion protein, used as the standard, were diluted with 0.1% BSA, 0.3 M sodium chloride, 0.05% Tween 20/PBS. When plasma was used as the sample for determination, plasma was diluted to five times or more. Each sample was added at 50 μL/well. After reaction for 2 hours at 37° C. with stirring, plate was washed five times with physiological saline containing 0.05% Tween 20. Biotin-labeled F1232-10-2 F(ab')2 antibody was diluted with PBS containing 20% Poly-HRP DILUENT (Fitzgerald), 0.3 M sodium chloride and 0.05% Tween 20, and 50 μL of this solution was added to each well. After reaction for 1 hour at 37° C. with stirring, plate was washed five times in the same manner. Then, POLY-HRP80-Streptavidin (Fitzgerald) was diluted with PBS containing 20% Poly-HRP DILUENT and 0.05% Tween 20, and 50 μL of this solution was added to each well. After reaction for 30 minutes at 37° C. with stirring, platelet was washed six times in the same manner, and TMB solution (BioFix) was added to each well. After reaction for 20 minutes at room temperature, the reaction was stopped with 0.5 M sulfuric acid solution. The absorbance at 450 nm was measured using a plate spectrophotometer (NJ-2100, Nippon InterMedic). FIG. 8 shows the standard curve using hGPVI-hFc fusion protein. This assay system has an absorbance difference of approximately 40 mAbs at 3 pg/mL of the standard, and the determination sensitivity was therefore 3 pg/mL or less.

Example 9

Preparation of Rat PRP and Stimulation of Platelets with Convulxin, CRP, or ADP

Citrated blood was collected from the normal rat, and platelet rich plasma (PRP) was prepared by centrifugation at 110×g for 15 minutes at 25° C. After adjusting the pH of the PRP to 6.5 with ACD-A (acid-citrate-dextrose), the platelets were recovered by centrifugation at 830×g for 10 minutes at 25° C. The recovered platelets were washed twice by the addition of HEPES buffer (137 mM NaCl, 1 mM $MgCl_2$, 5.5 mM glucose, 3 mM $NaH_2PO_4$, 10 mM HEPES, 1 mg/mL BSA) adjusted to pH 6.5 with ACD-A. After washing, the platelets were suspended by the addition of HEPES buffer (pH 7.3) to obtain washed platelets. Convulxin (Alexis), CRP (synthetic peptide), or ADP was added to the washed platelets in the presence of 1 mM $CaCl_2$ and 1 mM $MgCl_2$, and the platelets were stimulated for 1 hour at room temperature. The reaction was stopped by the addition of Protease Inhibitor Cocktail solution containing 25 mM EDTA, and this reaction mixture was followed by centrifugation at 18,000×g for 1 minute at 25° C., and a supernatant fraction and a platelet fraction were recovered.

Example 10

Flow Cytometric Determination of GPVI Expression of Rat Platelets

Figure 9:
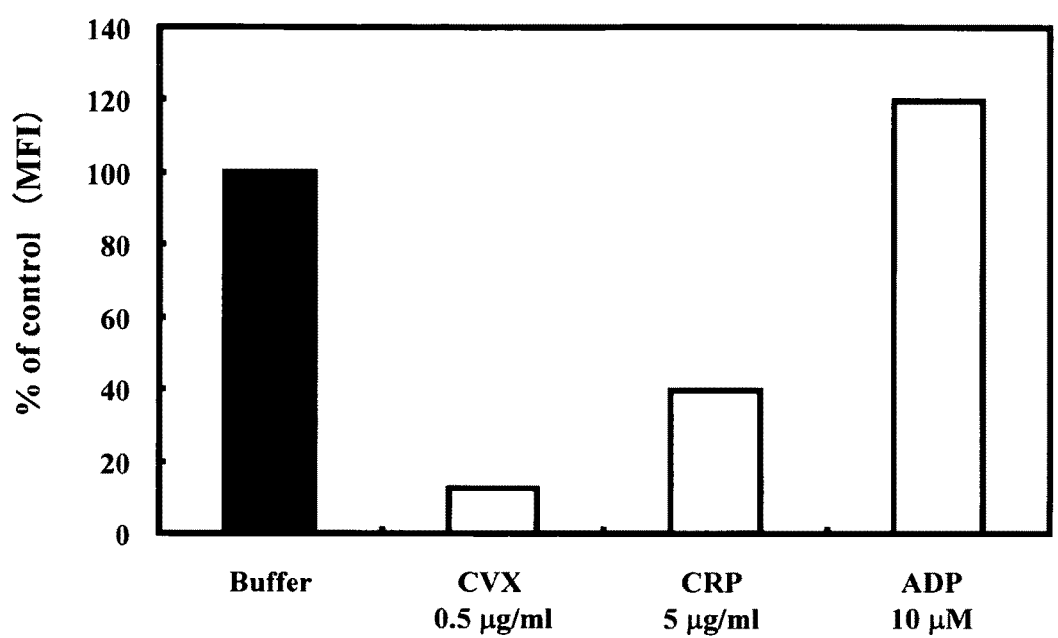
FIG. 9 shows the results of the flow cytometric analysis of GPVI on the rat platelet membrane.

Washed platelets were stimulated with convulxin, CRP, or ADP by the method described in Example 9. Washed platelets added with buffer only were served as the control, and the reaction mixture was stationary incubated for 1 hour at room temperature. After the reaction had been stopped by the addition of Protease Inhibitor Cocktail solution containing 25 mM EDTA, the stimulated platelets were washed with PBS containing 0.5% inactivated FBS and 2.5 mM EDTA (abbreviated below as FACS buffer). Then, 0.5 μg per $3\times10^5$ platelets of the mouse anti-rat GPVI antibody F1239-11-1 labeled with the fluorescent dye R-Phycoerythrin (PE) was added, and the mixture was stationary incubated for 30 minutes at room temperature in the dark. As an isotype control for the PE-labeled F1239-11-1, a sample was also prepared by the addition of the same quantity of PE-labeled mouse IgG2a κ antibody. After 30 minutes, the platelets were washed with FACS buffer and the quantity of GPVI expression on the membrane surface of the platelets was analyzed by determination of the fluorescent intensity of the platelets with a Cytomics FC500 flow cytometer (Beckman Coulter). The quantity of GPVI expression was calculated by subtracting the value obtained for the detection of PE-labeled mouse IgG2a κ antibody from the value obtained for the detection of PE-labeled F1239-11-1. The results are shown in FIG. 9. In comparison to the platelets added with buffer only, a substantial reduction in GPVI expression was observed for the convulxin (CVX)-stimulated platelets and the CRP-stimulated platelets, while no reduction in GPVI expression was seen for the ADP-stimulated platelets.

Example 11

Determination of the Quantity of Soluble GPVI in Rat PRP by ELISA

Figure 10:
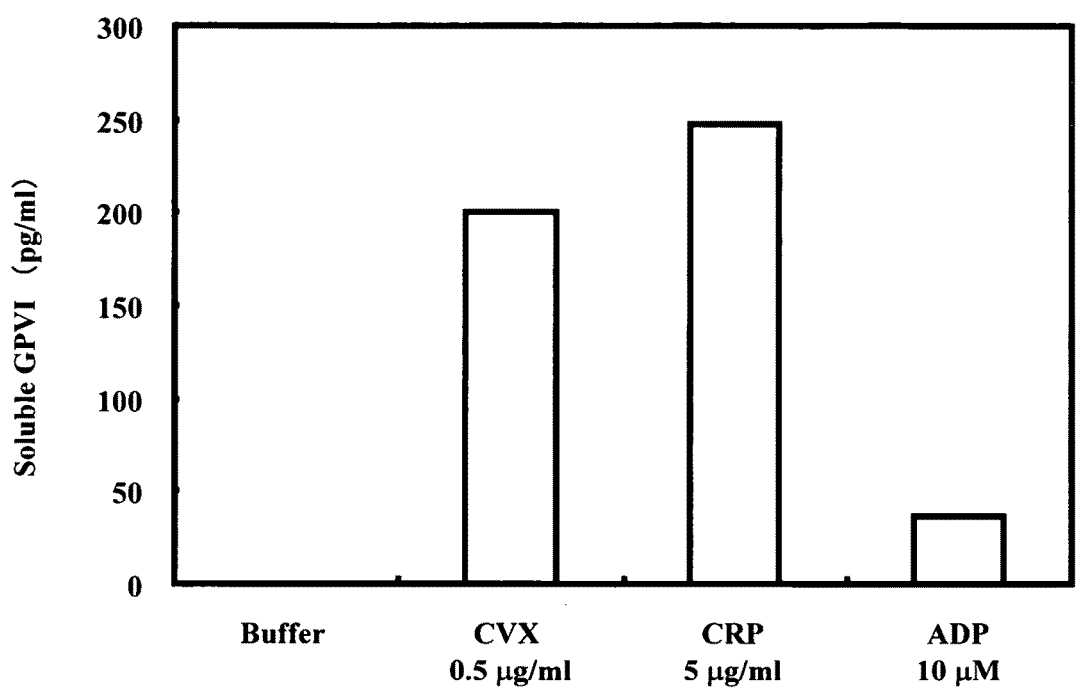
FIG. 10 shows the soluble GPVI concentration in the supernatant in rat platelet in vitro shedding samples.

In accordance with the method described in Example 9, washed platelets were stimulated with convulxin, CRP, or ADP and the supernatant fraction was recovered. The quantity of soluble GPVI in the supernatant was determined by the method described in Example 7. The results are shown in FIG. 10. A substantial increase in the quantity of soluble GPVI in the supernatant was observed for the platelets stimulated by convulxin and the platelets stimulated by CRP. On the other, increase in the quantity of soluble GPVI in the supernatant was weak for the platelets stimulated by ADP.

Example 12

Preparation of Monkey PRP and Stimulation of Platelets with Convulxin, CRP, and ADP Citrated blood was collected from the normal monkey, and platelet rich plasma (PRP) was obtained by centrifugation at 115×g for 15 minutes at 25° C. After adjusting the pH of the PRP to 6.5 with ACD-A (acid-citrate-dextrose), the platelets were recovered by centrifugation at 830×g for 10 minutes at 25° C. The recovered platelets were washed twice by the addition of HEPES buffer (137 mM NaCl, 1 mM $MgCl_2$, 5.5 mM glucose, 3 mM $NaH_2PO_4$, 10 mM HEPES, 1 mg/mL BSA) adjusted to pH 6.5 with ACD-A. After washing, the platelets were suspended by the addition of HEPES buffer (pH 7.3) to obtain washed platelets. Convulxin (Alexis), CRP (synthetic peptide), or ADP was added to the washed platelets in the presence of 1 mM $CaCl_2$ and 1 mM $MgCl_2$, and the platelets were stimulated for 1 hour at room temperature. The reaction was stopped by the addition of Protease Inhibitor Cocktail solution containing 25 mM EDTA, and this reaction mixture was followed by centrifugation at 18,000×g for 1 minute at 25° C. A supernatant fraction and a platelet fraction were recovered.

Example 13

Flow Cytometric Determination of GPVI Expression of Monkey Platelets

Figure 11:
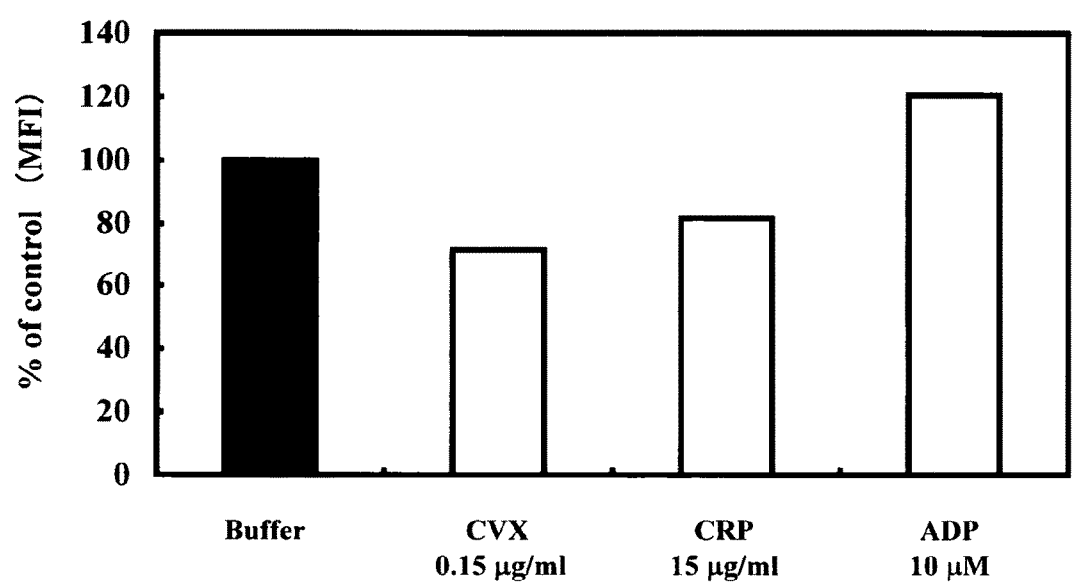
FIG. 11 shows the results of the flow cytometric analysis of GPVI on the monkey platelet membrane.

Washed platelets were stimulated with convulxin, CRP, or ADP by the method described in Example 12. Washed platelets added with buffer only were served as the control, and the reaction mixture was stationary incubated for 1 hour at room temperature. After the reaction had been stopped by the addition of Protease Inhibitor Cocktail solution containing 25 mM EDTA, the stimulated platelets were washed with FACS buffer. Then, 1 μg per $4 \times 10^5$ platelets of chimeric anti-human GPVI antibody F1232-37-2 labeled with the fluorescent dye PE or the PE-labeled chimeric anti-human GPVI antibody F1232-10-1 was added, and the reaction mixture was stationary incubated for 30 minutes at room temperature in the dark. As an isotype control for the PE-labeled chimeric F1232-37-2 and the PE-labeled chimeric F1232-10-1, a sample was also prepared by the addition of the same quantity of PE-labeled human IgG4 antibody. After 30 minutes, the platelets were diluted with FACS buffer and the quantity of GPVI expression on the membrane surface of the platelets was analyzed by determination of the fluorescent intensity of the platelets with a Cytomics FC500 flow cytometer (Beckman Coulter). The quantity of GPVI expression was calculated by subtracting the value obtained for the detection of PE-labeled human IgG4 antibody from the value obtained for the detection of PE-labeled chimeric F1232-37-2 or PE-labeled chimeric F1232-10-1. The results are shown in FIG. 11. In comparison to the platelets added with buffer only, a reduction in GPVI expression was observed for the convulxin (CVX)-stimulated platelets and the CRP-stimulated platelets, while no reduction in GPVI expression was seen for the ADP-stimulated platelets.

Example 14

Determination of the Quantity of Monkey Platelet GPVI by Western Blotting

Figure 12:
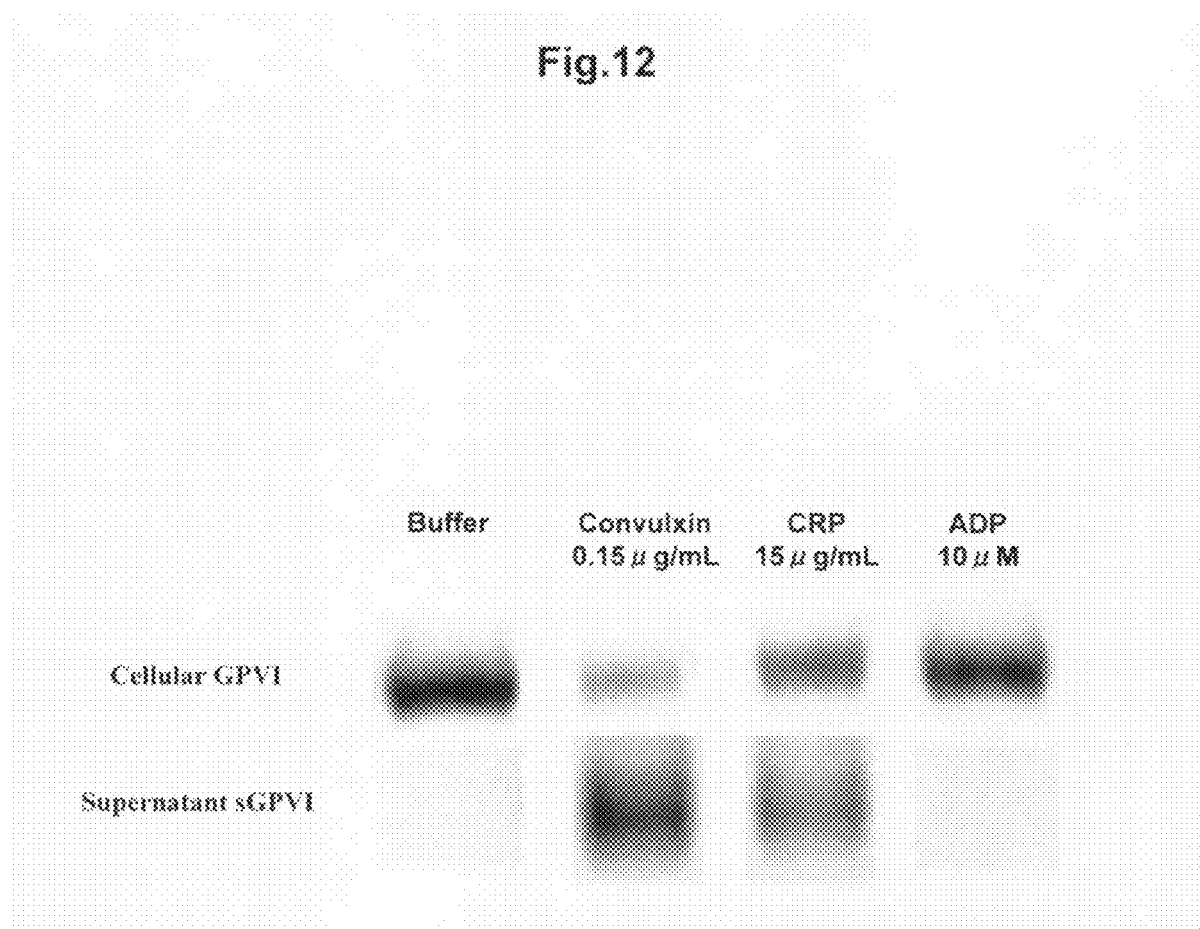
FIG. 12 shows the results of GPVI western analysis of monkey platelets.

Using the method described in Example 12, washed platelets were stimulated with convulxin, CRP, or ADP. Then, a supernatant fraction and a platelet fraction were recovered. The soluble GPVI present in the supernatant fraction and the GPVI present in the platelet fraction (referred to hereafter as platelet GPVI) were detected by western blotting. In brief, 4 μL of 4× Sample Buffer (+β-mercaptoethanol, Protease Inhibitor Cocktail (Roche), Phosphatase Inhibitor Cocktail (Pierce)) was added to 12 μL of the supernatant fraction. In the case of the platelet fraction, 1 μL of 1× Sample Buffer (+β-mercaptoethanol, Protease Inhibitor Cocktail (Roche), Phosphatase Inhibitor Cocktail (Pierce)) per $1.9 \times 10^6$ platelets was added to the platelet fraction, and sample was heated for 5 minutes at 99° C. The heat-treated sample was applied to a 5 to 20% concentration gradient polyacrylamide gel (ATTO), using the entire amount per lane for the supernatant fraction and 16 μL per lane for the platelet fraction. Then, electrophoresis was performed at a constant current of 30 mA per gel. According to the standard blotting procedure, the gel was blotted onto a low-fluorescence membrane (Immobilon-FL, PVDF, Millipore) by the semi-dry method. After blotting, the membrane was blocked with BlockAce (Dainippon Pharmaceutical Co., Ltd.) overnight at 4° C. After blocking, the primary antibody (polyclonal antibody prepared using human GPVI synthetic peptide as an antigen), diluted with PBS containing 10% BlockAce/0.1% Tween 20 (TPBS), was added and the membrane was incubated for 1 hour at room temperature. After washing with TPBS, the secondary antibody ( anti-rabbit Igs HRP), diluted with 10% BlockAce/TPBS, was added and the membrane was incubated for 30 minutes at room temperature. After washing with TPBS, the soluble GPVI and platelet GPVI were detected using ECL Plus (Amersham Biosciences) and Typhoon9410 (Amersham Biosciences). The results are shown in FIG. 12. A substantial reduction of platelet GPVI was observed in the convulxin-stimulated platelets and the CRP-stimulated platelets. In addition, a substantial increase in soluble GPVI was observed in the convulxin-stimulated platelets and the CRP-stimulated platelets. In the case of the ADP-stimulated platelets, on the other hand, no substantial change in the expression level of platelet GPVI was observed, and soluble GPVI was not detected.

Example 15

Determination of the Quantity of Soluble GPVI in Monkey PRP by ELISA

Figure 13:
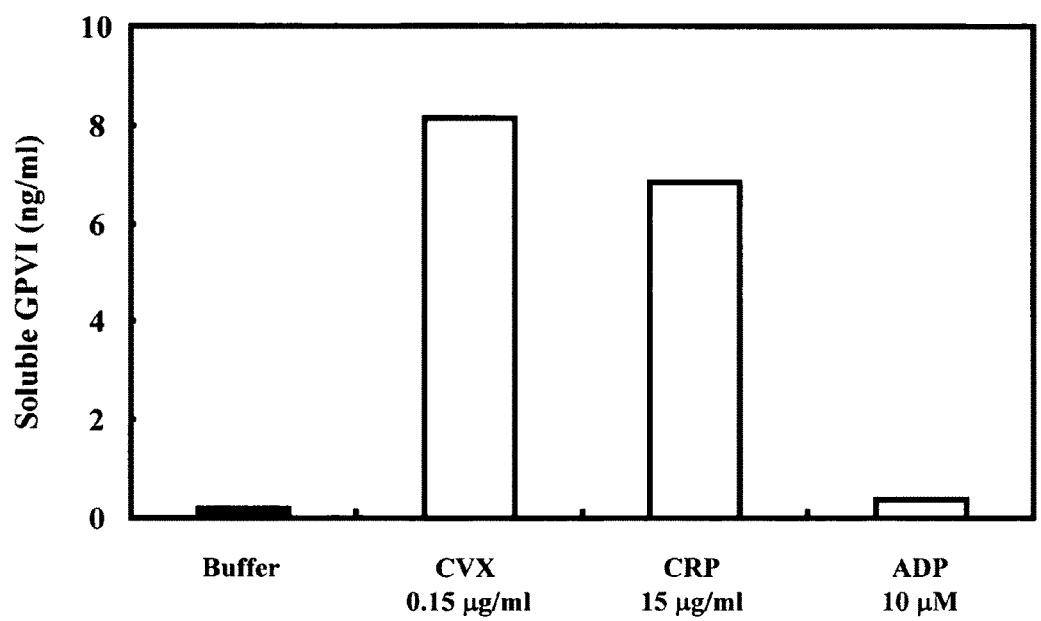
FIG. 13 shows the soluble GPVI concentration in the supernatant in monkey platelet in vitro shedding samples.

In accordance with the method described in Example 12, washed platelets were stimulated with convulxin, CRP, or ADP and the supernatant was recovered. The quantity of soluble GPVI in the supernatant was determined by the method described in Example 8. The results are shown in FIG. 13. A substantial increase in the quantity of soluble GPVI in the supernatant was observed for the platelets stimulated by convulxin and the platelets stimulated by CRP. On the other, the increase in the quantity of soluble GPVI in the supernatant was very weak for the platelets stimulated by ADP.

Example 16

Preparation of Human PRP and Stimulation of Platelets with Collagen, Convulxin, CRP, or ADP Citrated blood was collected from the normal human, and platelet rich plasma (PRP) was obtained by centrifugation at 170×g for 15 minutes at 25° C. After adjusting the pH of the PRP to 6.5 with ACD-A (acid-citrate-dextrose), the platelets were recovered by centrifugation at 830×g for 10 minutes at 25° C. The recovered platelets were washed twice by the addition of HEPES buffer (137 mM NaCl, 1 mM MgCl$_2$, 5.5 mM glucose, 3 mM NaH$_2$PO$_4$, 10 mM HEPES, 1 mg/mL BSA) adjusted to pH 6.5 with ACD-A. After washing, the platelets were suspended by the addition of HEPES buffer (pH 7.3) to obtain washed platelets. Collagen (Horm collagen reagent, Nycomed), convulxin (Alexis), CRP (synthetic peptide), or ADP was added to the washed platelets in the presence of 1 mM CaCl$_2$ and 1 mM MgCl$_2$, and the platelets were stimulated for 1 hour at room temperature. The reaction was stopped by the addition of Protease Inhibitor Cocktail solution containing 25 mM EDTA, and this reaction mixture was followed by centrifugation at 18,000×g for 1 minute at 25° C. A supernatant fraction and a platelet fraction were recovered.

Example 17

Flow Cytometric Determination of GPVI Expression of Human Platelets

Figure 14:
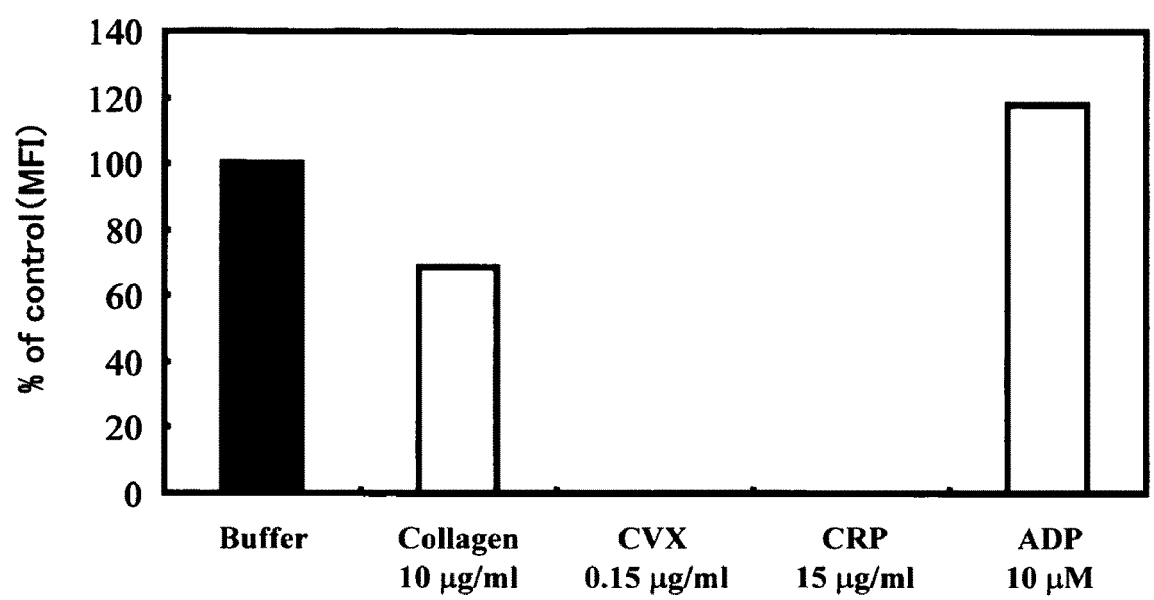
FIG. 14 shows the results of the flow cytometric analysis of GPVI in human platelets.

Washed platelets were stimulated with collagen, convulxin, CRP, or ADP by the method described in Example 16. Washed platelets added with buffer only were served as the control, and the reaction mixture was stationary incubated for 1 hour at room temperature. After the reaction had been stopped by the addition of Protease Inhibitor Cocktail solution containing 25 mM EDTA, the stimulated platelets were washed with FACS buffer. Then, 1 μg per $4 \times 10^5$ platelets of chimeric anti-human GPVI antibody F1232-37-2 labeled with the fluorescent dye PE was added, and the mixture was stationary incubated for 30 minutes at room temperature in the dark. As an isotype control for the PE-labeled chimeric F1232-37-2, a sample was also prepared by the addition of the same quantity of PE-labeled human IgG4 antibody. After 30 minutes, the platelets were diluted with FACS buffer and the quantity of GPVI expression on the membrane surface of the platelets was analyzed by determination of the fluorescent intensity of the platelets with a Cytomics FC500 flow cytometer (Beckman Coulter). The quantity of GPVI expression was calculated by subtracting the value obtained for the detection of PE-labeled human IgG4 antibody from the value obtained for the detection of PE-labeled chimeric F1232-37-2. The results are shown in FIG. 14. A decline of GPVI expression level was observed for the collagen-stimulated platelets. GPVI expression was almost depleted for the convulxin-stimulated platelets and the CRP-stimulated platelets. On the other hand, a decline of GPVI expression level was not observed for the ADP-stimulated platelets.

Example 18

Determination of the Quantity of Human Platelet GPVI by Western Blotting

Figure 15:
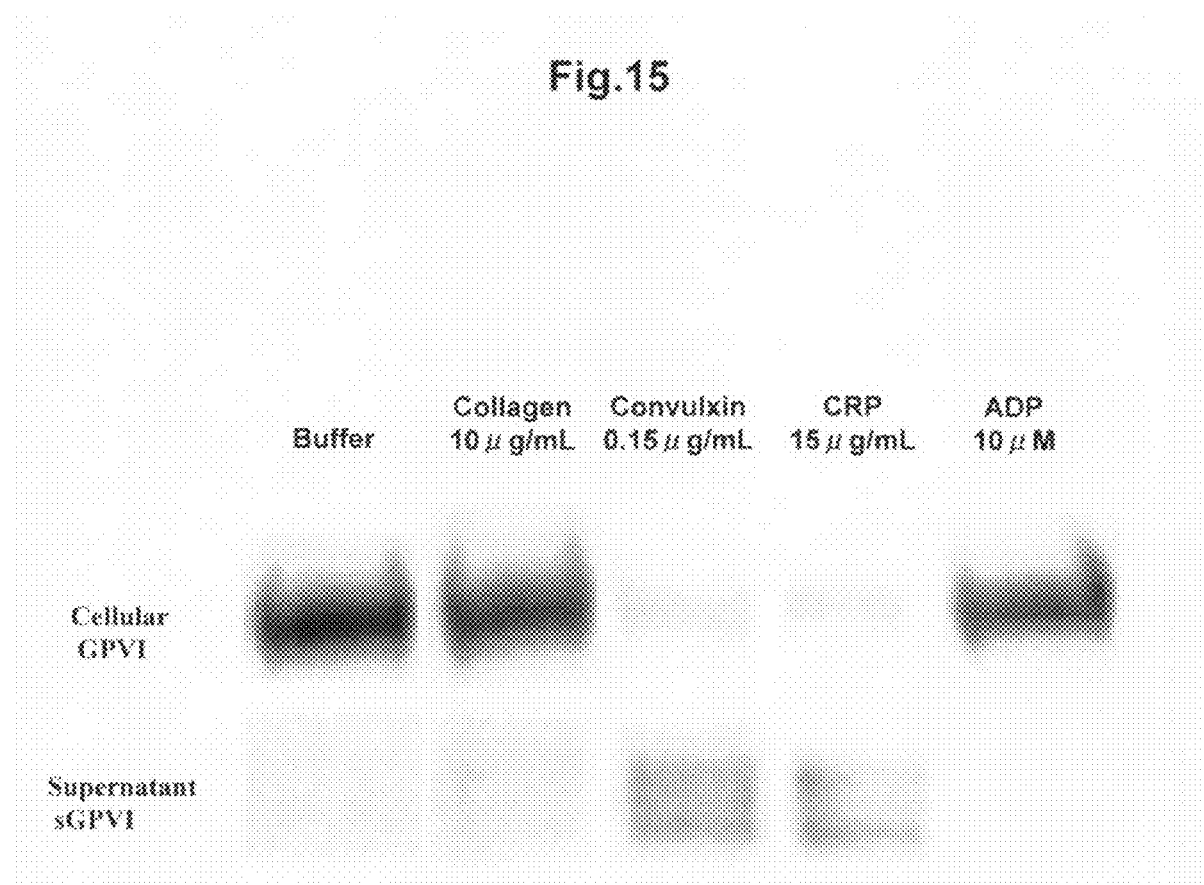
FIG. 15 shows the results of GPVI western analysis of human platelets.

Using the method described in Example 16, washed platelets were stimulated with collagen, convulxin, CRP, or ADP. Then, a supernatant fraction and a platelet fraction were recovered. The soluble GPVI present in the supernatant fraction and the GPVI present in the platelet fraction (referred to hereafter as platelet GPVI) were detected by western blotting. In brief, 4 µL of 4× Sample Buffer (+β-mercaptoethanol, Protease Inhibitor Cocktail (Roche), Phosphatase Inhibitor Cocktail (Pierce)) was added to 12 µL of the supernatant fraction. In the case of the platelet fraction, 1 µL of 1× Sample Buffer (+β-mercaptoethanol, Protease Inhibitor Cocktail (Roche), Phosphatase Inhibitor Cocktail (Pierce)) per $1.9 \times 10^6$ platelets was added to the platelet fraction, and sample was heated for 5 minutes at 99° C. The heat-treated sample was applied to a 5 to 20% concentration gradient polyacrylamide gel (ATTO), using the entire amount per lane for the supernatant fraction and 16 µL per lane for the platelet fraction. Then, electrophoresis was performed with a constant current of 30 mA per gel. According to the standard blotting procedure, the gel was blotted onto a low-fluorescence membrane (Immobilon-FL, PVDF, Millipore) by the semi-dry method. After blotting, the membrane was blocked with BlockAce (Dainippon Pharmaceutical Co., Ltd.) overnight at 4° C. After blocking, the primary antibody (polyclonal antibody prepared using human GPVI synthetic peptide as an antigen), diluted with PBS containing 10% BlockAce/0.1% Tween 20 (TPBS), was added and the membrane was incubated for 1 hour at room temperature. After washing with TPBS, the secondary antibody (anti-rabbit Igs HRP), diluted with 10% BlockAce/TPBS, was added and the membrane was incubated for 30 minutes at room temperature. After washing with TPBS, the soluble GPVI and platelet GPVI were detected using ECL Plus (Amersham Biosciences) and Typhoon9410 (Amersham Biosciences). The results are shown in FIG. 15. A substantial reduction of platelet GPVI was observed in the convulxin-stimulated platelets and the CRP-stimulated platelets. In addition, a substantial increase in soluble GPVI was observed in the collagen-stimulated platelets, the convulxin-stimulated platelets and the CRP-stimulated platelets. In the case of the ADP-stimulated platelets, on the other hand, no substantial change in platelet GPVI was observed, and soluble GPVI was not detected.

Example 19

Determination of the Quantity of Soluble GPVI in Human PRP by ELISA

Figure 16:
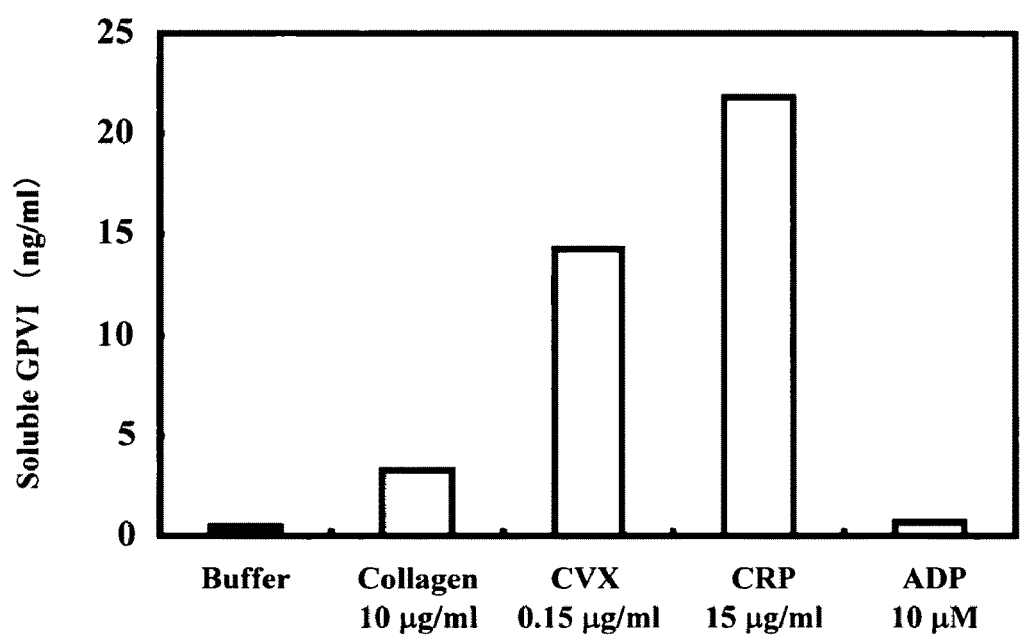
FIG. 16 shows the soluble GPVI concentration in the supernatant in human platelet in vitro shedding samples.

In accordance with the method described in Example 16, washed platelets were stimulated with collagen, convulxin, CRP, or ADP and the supernatant was recovered. The quantity of soluble GPVI in the supernatant was determined by the method described in Example 8. The results are shown in FIG. 16. A substantial increase in the quantity of soluble GPVI in the supernatant was observed for the platelets stimulated by collagen, the platelets stimulated by convulxin, and the platelets stimulated by CRP. On the other, an increase in the soluble GPVI in the supernatant was not observed in the platelets stimulated by ADP.

Example 20

Determination of the Quantity of Soluble GPVI in Plasma in Rat Endotoxin-Induced Thrombosis Model Female Wistar rats were anesthetized with pentobarbital sodium (50 mg/kg). Endotoxin (a dose of 20 mg/kg in 2 hours or a dose of 40 mg/kg in 4 hours) was intravenously infused via right femoral vein. After the completion of endotoxin infusion, blood was collected from the abdominal aorta and the platelet count was determined using an automated hemocytometer (Sysmex, Toa Medical Electronics). In addition, the plasma was separated by centrifugation of the blood and the soluble GPVI was determined by the method described in Example 7 and the soluble ICAM-1 was determined using an ELISA kit (R & D System, Rat sICAM-I (CD54) Immunoassay). The results are shown in FIG. 17. A decline in the platelet count was observed by the administration of endotoxin. It indicates that platelet is activated by endotoxin administration. In addition, the quantity of soluble GPVI and soluble ICAM-1 in the plasma were increased by endotoxin administration.

Example 21

Figure 18:
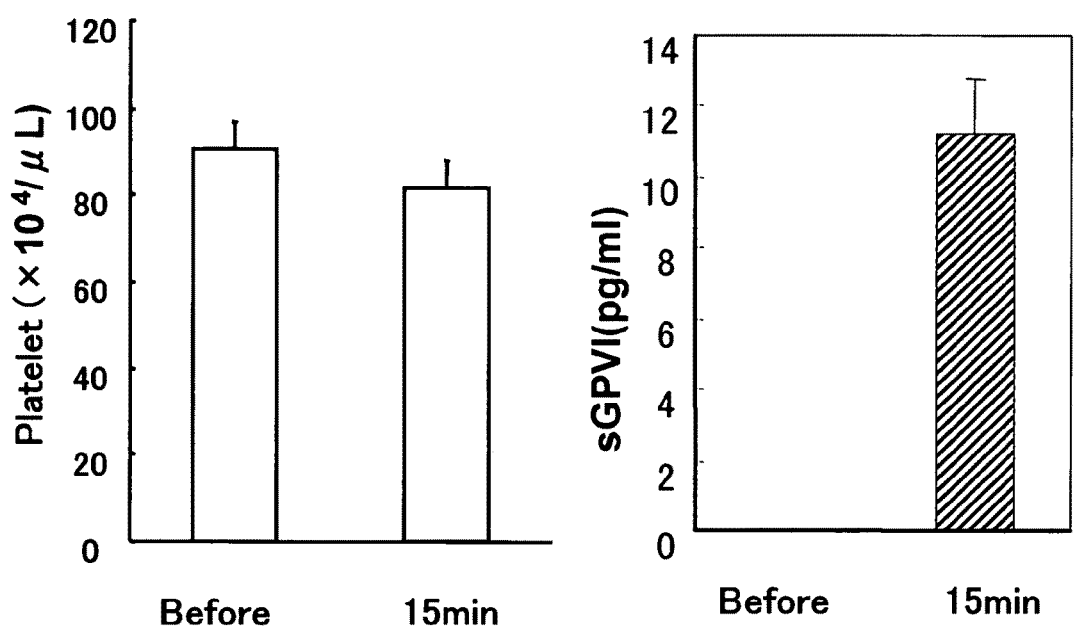
FIG. 18(A) shows experimental results after 30 minutes in rat collagen-induced thrombosis model.
FIG. 18(B) shows experimental results after 15 minutes in rat collagen-induced thrombosis model.

(1) Determination of the Quantity of Soluble GPVI in Plasma in Rat Collagen-Induced Thrombosis Model Male SD rats were anesthetized with pentobarbital sodium (50 mg/kg) and collagen (a dose of 0.5 mg/kg in 15 minutes) was intravenously infused via right femoral vein. At 30 minutes after the start of collagen infusion, blood was collected from the jugular vein and the platelet count was determined using an automated hemocytometer (Sysmex, Toa Medical Electronics). In addition, the plasma was separated by centrifugation of the blood and the soluble GPVI was determined by the method described in Example 7 and the soluble ICAM-1 was determined using an ELISA kit (R & D System, Rat sICAM-1 (CD54) Immunoassay). The results are shown in FIG. 18(A). A decline in the platelet count was observed by the administration of collagen. It indicates that platelet is activated by collagen administration. In addition, the quantity of soluble GPVI and soluble ICAM-1 in the plasma were increased by collagen administration. The degree of the decline in the platelet count agreed with the degree of the increase in the quantity of soluble GPVI in the plasma.

In the same manner, male SD rats were anesthetized with pentobarbital sodium (50 mg/kg) and collagen (a dose of 0.1 mg/kg) was rapidly administered via right femoral vein. Blood was collected from the jugular vein at 15 minutes, 30 minutes, and 60 minutes post-collagen administration and the platelet count was determined using an automated hemocytometer (Sysmex, Toa Medical Electronics). In addition, the plasma was separated by centrifugation of the blood and the soluble GPVI was determined by the method described in Example 7. The results are shown in FIG. 18(B). While the decline in the platelet count was slight, quantity of soluble GPVI in the plasma was rapidly increased at 15 minutes after collagen administration.

(2) Effect of GPVI Antibody in Rat Collagen-Induced Thrombosis Model

Anti-rat GPVI antibody (F1239-6-1) was administered to male SD rats. After 6 days, collagen was rapidly and intravenously administered at a dose of 0.8 mg/kg. The mortality was observed from post-collagen administration to 15 minutes. The results are shown in Table 4. The anti-rat GPVI antibody (F1239-6-1) completely prevented animal death at a dose of 0.3 mg/kg in an animal thrombosis model in which the quantity of soluble GPVI in the plasma undergoes elevation.

Therefore, determination of the sGPVI in plasma by the determination method of the present invention enables the detection, determination, or quantitation of platelet activation or vascular endothelial injury prior to disease onset; enables the diagnosis of diseases associated with platelet activation or vascular endothelial injury, such as thrombosis and so forth; and enables the selection of patients for treatment. In addition, a high rate of effectiveness will presumably be obtained for the administration of an antiplatelet drug, e.g., an anti-GPVI antibody, to such patients.

TABLE 4

| group | number of survivors/number of animals |
| --- | --- |
| physiological saline | 0/15 |
| F1239-6-1 0.1 mg/kg | 1/7 |
| F1239-6-1 0.3 mg/kg | 7/7 |
| F1239-6-1 1.0 mg/kg | 8/8 |

Example 22

Figure 19:
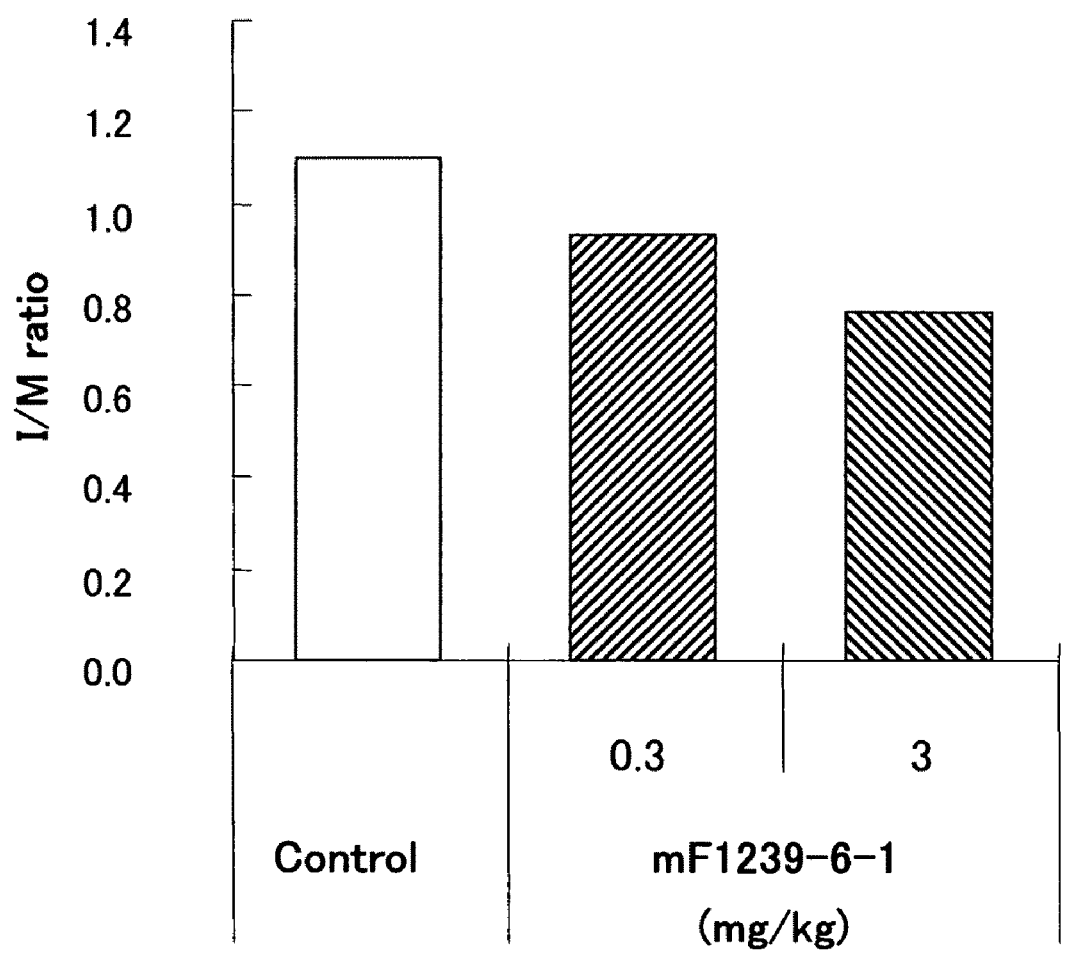
FIG. 19(A) shows the experimental results of the determination of the soluble GPVI in plasma, using a balloon catheter-induced vascular intimal injury model.
FIG. 19(B) shows the effect of anti-GPVI antibody using a balloon catheter-induced vascular intimal injury model.

(1) Determination of the Quantity of Soluble GPVI in the Plasma in Rat Balloon Injury Model Male SD rats were anesthetized by the intraperitoneal administration of 45 mg/kg pentobarbital sodium and the neck region and femoral region were exposed. A balloon catheter was inserted into the femoral artery and the tip was extended as far as the internal/external carotid artery branch of the left carotid artery. After it had been confirmed that the balloon catheter was in the carotid artery, the balloon was inflated by introducing air into the balloon. With the balloon inflated, the catheter was withdrawn to the aortic arch. This process was carried out three times in order to injure the endothelial intima. On the following day, citrated blood was collected from the abdominal aorta under anesthesia by the intraperitoneal administration of 45 mg/kg pentobarbital sodium and the plasma was recovered. The quantity of soluble GPVI in the plasma was determined by the method described in Example 7 and the soluble ICAM-1 was determined using an ELISA kit (R & D System, Rat sICAM-1 (CD54) Immunoassay). The results are shown in FIG. 19(A). The amount of soluble ICAM-1 in the plasma was increased by injury to the endothelial intima using the balloon catheter. It indicated that the endothelial intima was injured by the balloon catheter. Increase in the quantity of soluble GPVI was also observed.

(2) Effect of Anti-GPVI Antibody in Rat Balloon Injury Animal Model

The effect of anti-rat GPVI antibody in the animal model described in Example 22 was examined. In brief, 3 mg/kg F1239-6-1 was administered subcutaneously, and the vascular intima was injured at 6 days after the administration using the method of Example 22. Fifteen days after the balloon injury, the right and left carotid arteries were collected under anesthesia by pentobarbital and were fixed in 10% neutral buffered formalin, and paraffin blocks were prepared. Then, the paraffin blocks were thin sectioned to prepare the specimens. After staining with hematoxylin-eosin, the specimens were observed under a microscope. The observed image was recorded as a digital image using a CCD camera and analyzed using WinROOF image analysis software to calculate the cross-sectional areas of the intima and the media. The results are shown in FIG. 19(B). The anti-rat GPVI antibody (F1239-6-1) inhibited intimal thickening in an animal arteriosclerosis model that presented an increase in soluble GPVI in the plasma.

Therefore, the determination of the sGPVI in plasma by the determination method of the present invention enables the detection, determination, or quantitation of platelet activation or vascular endothelial injury prior to disease onset; enables the diagnosis of diseases associated with platelet activation or vascular endothelial injury, such as arteriosclerotic diseases and so forth; and enables the selection of patients for treatment. In addition, a high rate of effectiveness will presumably be obtained for the administration of an antiplatelet drug, e.g., an anti-GPVI antibody, to such patients.

Example 23

Figure 20:
FIG. 20 shows the change in soluble GPVI in the urine in rat endotoxin-induced thrombosis model.

Measurement of the Quantity of Soluble GPVI in the Urine in Rat Endotoxin-Induced Thrombosis Model Female Wistar rats were anesthetized with pentobarbital sodium (50 mg/kg) and endotoxin (40 mg/kg in 4 hours) was intravenously infused via right femoral vein. After the completion of endotoxin infusion, urine was collected and the soluble GPVI in the urine was determined using the method described in Example 7. The results are shown in FIG. 20. Increase in the quantity of soluble GPVI in the urine was also observed by the administration of endotoxin.

Example 24

Figure 21:
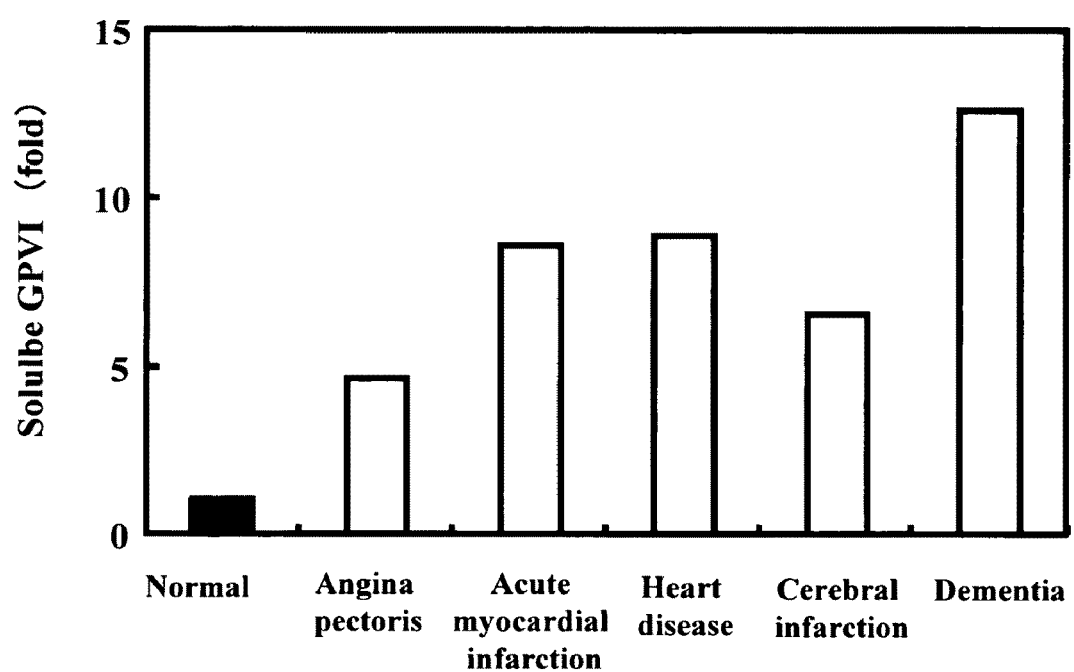
FIG. 21 shows the quantity of soluble GPVI in the plasma for various human pathologies.

Determination of the Quantity of Soluble GPVI in the Plasma in Various Human Pathologies The quantity of soluble GPVI in the plasma was determined by the method described in Example 8 for various human pathologies. The results are shown in FIG. 21. The plasma from patients with angina pectoris, acute myocardial infarction, heart disease, cerebral infarction, and dementia had higher soluble GPVI values than the plasma from normal individuals.

Example 25

Preparation of Anti-Human GPVI Monoclonal Antibodies

20 μg purified hGPVI-mFc was mixed with Freund's complete adjuvant (Difco) or alum (Pierce) and oligo CpG to provide the antigen for administration. ddY mice (female, 8 weeks, SLC) was injected twice, and after 3 days lymphocytes were isolated from the lymph nodes or spleen. The obtained lymphocytes were mixed with P3×63-Ag.8.U1 (ATTC) and cell fusion was then carried out using polyethylene glycol (PEG1500, Sigma) according to *Introduction to*

*Monoclonal Antibody Experimental Procedures*, Tamie ANDO and Takeshi CHIBA (Kodansha), page 83. The hybidomas were selected using HAT culture medium, and after 1 week Hybidomas producing the desired antibody were screened by the binding activity to hGPVI-hFc and hGPVI-mL9-hFc as the indicator. In brief, purified hGPVI-hFc or hGPVI-mL9-hFc was diluted to 1 μg/mL with D-PBS (pH 7.4). This solution was added to immunoplate (Maxisorb, NUNC) at 50 μL/well. Immobilization was carried out using the same method as described in Example 6. Culture supernatant was subsequently added to each well, and plate was incubated for 1 hour at room temperature. Then, using the same method as described in Example 6, peroxidase-labeled anti-mouse immunoglobulin antibody (Dako, P260) was added, and the absorbance was measured. As a result, cells were selected that produced antibody that underwent binding (absorbance at least 1) with purified hGPVI-hFc but that did not bind (absorbance 0.5 or less) to hGPVI-mL9-hFc. These antibody producing hybridomas were cloned by a standard method. The same screening was carried out after 8 to 10 days to obtain hybridomas that produced L9-specific mouse anti-human GPVI antibody. The obtained hybridomas were cultured, and the monoclonal antibodies were purified as described in Experiment 4. The GPVI binding activity of each antibody is shown (Table 5), assigning − to an absorbance of 0.5 or less in the aforementioned ELISA system, + to an absorbance of 0.5 up to 1.0, ++ to an absorbance of 1.0 to 2.0, and +++ to an absorbance greater than 2.0.

The same procedure was used to obtain L2-specific mouse anti-human GPVI antibody hybridomas (F1232-10-1 and F1232-10-2, which was considered to originate from the same clone).

TABLE 5

| clone | binding with hGPVI-hFc | binding with hGPVI-mL9-hFc |
| --- | --- | --- |
| F1249-18-2 | +++ | − |
| F1245-7-1 | ++ | − |
| F1246-1-1 | ++ | − |
| F1249-5-1 | ++ | − |
| F1249-20-1 | +++ | − |
| F1249-24-1 | +++ | − |
| F1249-30-1 | +++ | − |
| F1245-5-1 | ++ | − |
| F1245-6-2 | ++ | − |
| F1249-3-2 | + | − |
| F1245-4-1 | +++ | − |
| F1249-22-1 | + | − |
| F1232-37-2 | ++ | − |

Example 26

Determination of the Variable Region Amino Acid Sequences of Anti-GPVI Antibodies Single-strand cDNA was synthesized from hybridomas F1232-37-2 and F1232-10-1 by the standard methods. The DNA encoding the variable regions of the anti-GPVI antibodies was amplified by PCR using Mouse Ig-Primer Set (Novagen) and single-strand cDNA as the template, and the nucleotide sequence was determined. The nucleotide sequence and putative amino acid sequence of the heavy-chain and light-chain variable regions of the monoclonal antibodies F1232-37-2 and F1232-10-1 secreted from each hybridomas, are shown in sequence table (SEQ ID NO: 18-25).

Example 27

Confirmation of the Ability of the Anti-GPVI Antibodies to Recognize Human Soluble GPVI Convulxin or buffer only (control) was added to washed platelets prepared from normal humans by the method described in Example 16, and a supernatant fraction was recovered after stationary incubation for 1 hour at 37° C. According to the method in Example 18, human soluble GPVI was detected by western blotting using mouse anti-human GPVI antibodies (F1232-7-1 or F1232-10-2) and polyclonal antibody (prepared using human GPVI synthetic peptide as an antigen), as the primary antibodies. The results are shown in FIG. 22. F1232-7-1 and F1232-10-2 were able to identify the presence of human soluble GPVI in the supernatant fraction sample from convulxin-stimulated washed platelets in the same manner as the polyclonal antibody prepared from human GPVI synthetic peptide as an antigen. Moreover, in the case of the supernatant fraction sample from the buffer-added washed platelets, human soluble GPVI was not detected by F1232-7-1 or F 1232-10-2 or the polyclonal antibody prepared from human GPVI synthetic peptide as an antigen. It indicates that F1232-7-1 and F1232-10-2 used in the ELISA system for human soluble GPVI, recognize human soluble GPVI.

INDUSTRIAL APPLICABILITY

GPVI in a sample, and particularly sGPVI or mGPVI in a biological sample, can be measured at high sensitivities by the determination method, determination reagent, or kit of the present invention. In addition, the detection, determination, or quantitation of sGPVI or mGPVI using the determination method, determination reagent, or kit of the present invention enables, inter alia, the detection, determination, quantitation, assessment, or evaluation of platelet activation or vascular endothelial injury; the diagnosis of diseases associated with platelet activation or vascular endothelial injury, the assessment of susceptibility to diseases associated with platelet activation or vascular endothelial injury, and the evaluation of the risk of onset of diseases associated with platelet activation or vascular endothelial injury; the selection of patients who respond to an antiplatelet drug, particularly an anti-GPVI antibody; the decision of the time of (beginning) the administration of such drugs; and the prediction, monitoring, or prognostic assessment of the therapeutic effects of, or the manifestation of side effects by, the antiplatelet drugs.

Sequence Listing Free Text

Sequence No. 1 is the sequence of a primer used in the PCR reactions in Example 1.
Sequence No. 2 is the sequence of a primer used in the PCR reactions in Example 1.
Sequence No. 3 is the sequence of a primer used in the PCR reactions in Example 1.
Sequence No. 4 is the sequence of a primer used in the PCR reactions in Example 1.
Sequence No. 5 is the sequence of a primer used in the PCR reactions in Example 1.
Sequence No. 6 is the sequence of a primer used in the PCR reactions in Example 1.
Sequence No. 7 is the sequence of a primer used in the PCR reactions in Example 1.
Sequence No. 8 is the sequence of a primer used in the PCR reactions in Example 1.

Sequence No. 9 is the sequence of a primer used in the PCR reactions in Example 1.
Sequence No. 10 is the sequence of a primer used in the PCR reactions in Example 1.
Sequence No. 11 is the sequence of a primer used in the PCR reactions in Example 1.
Sequence No. 12 is the sequence of a primer used in the PCR reactions in Example 1.
Sequence No. 13 is the sequence of a primer used in the PCR reactions in Example 1.
Sequence No. 14 is the sequence of a primer used in the PCR reactions in Example 1.
Sequence No. 15 is the sequence of a primer used in the PCR reactions in Example 2.
Sequence No. 16 is the sequence of a primer used in the PCR reactions in Example 2.
Sequence No. 17 is the sequence of a primer used in the PCR reactions in Example 2.

The invention claimed is:

1. A method of determining soluble GPVI (sGPVI) in a human body fluid using two or more anti-GPVI antibodies or fragments thereof having different binding sites, comprising:
   1) obtaining a sample that is a sample of a human body fluid or a sample prepared from a human body fluid;
   2) removing platelets from the sample, if the sample is a platelet containing sample;
   3) contacting the sample with a first anti-GPVI antibody or fragment thereof;
   4) contacting said sample with a second anti-GPVI antibody or fragment thereof, wherein the second antibody or fragment thereof has a GPVI binding site different from that of the first antibody or fragment thereof; and
   5) determining a value of soluble GPVI (sGPVI) in said sample based on said contacting with the first anti-GPVI antibody or fragment thereof and said contacting with the second anti-GPVI antibody or fragment thereof,
wherein at least two of anti-GPVI antibodies or fragments thereof selected from said two or more anti-GPVI antibodies or fragments thereof specifically bind loop 9 or loop 11 in GPVI domain 2, and loop 2 or loop 5 in GPVI domain 1 respectively.

2. The method of determination according to claim 1, further comprising the step of comparing the determined value of the soluble GPVI (sGPVI) in said sample with a standard curve for human soluble GPVI.

3. The method of determination according to claim 1, wherein the sensitivity of the determination is 30 pg/mL or less.

4. The method of determination according to claim 1, wherein the anti-GPVI antibody or fragment thereof that specifically binds loop 2 or loop 5 in GPVI domain 1 is the anti-GPVI antibody or fragment thereof that specifically binds loop 2; and
   the anti-GPVI antibody or fragment thereof that specifically binds loop 9 or loop 11 in GPVI domain 2 is the anti-GPVI antibody or fragment thereof that specifically binds loop 9.

5. The method of determination according to claim 1, wherein the first anti-GPVI antibody or fragment thereof is used as an immobilized antibody.

6. The method of determination according to claim 1, that is a sandwich immunoassay method.

7. A method of detecting, determining or quantitating platelet activation or aggregation, using anti-GPVI antibodies or fragments thereof, comprising:
   1) obtaining from a subject in need thereof a sample that is a sample of a human body fluid or a sample prepared from a human body fluid;
   2) removing platelets from the sample, if the sample is a platelet containing sample;
   3) contacting the sample with a first anti-GPVI antibody or fragment thereof;
   4) contacting said sample with a second anti-GPVI antibody or fragment thereof, wherein the second antibody or fragment thereof has a GPVI binding site different from that of the first antibody or fragment thereof;
   5) detecting, determining, or quantitating a value of sGPVI in said sample based on said contacting with the first anti-GPVI antibody or fragment thereof and said contacting with the second anti-GPVI antibody or fragment thereof; and
   6) comparing the determined value with
      a standard value of normal or healthy individuals to detect, determine or quantitate platelet activation or aggregation in the sample of the subject;
wherein the first and the second anti-GPVI antibodies or fragments thereof specifically bind loop 9 or loop 11 in GPVI domain 2; and loop 2 or loop 5 in GPVI domain 1.

8. The method of claim 7, wherein the platelet activation is caused by vascular endothelial injury or arteriosclerosis.

9. A method of diagnosing a disease caused by vascular endothelial injury or arteriosclerosis, a susceptibility to the disease caused by vascular endothelial injury or arteriosclerosis or a risk of developing the disease caused by vascular endothelial injury or arteriosclerosis using anti-GPVI antibodies or fragments thereof, comprising:
   1) obtaining from a subject in need thereof a sample that is a sample of a human body fluid or a sample prepared from a human body fluid;
   2) removing platelets from the sample, if the sample is a platelet containing sample;

3) contacting the sample with a first anti-GPVI antibody or fragment thereof;

4) contacting said sample with a second anti-GPVI antibody or fragment thereof, wherein the second antibody or fragment thereof has a GPVI binding site different from that of the first antibody or fragment thereof;

5) detecting, determining, or quantitating a value of sGPVI in said sample based on said contacting with the first anti-GPVI antibody or fragment thereof and said contacting with the second anti-GPVI antibody or fragment thereof; and 6) comparing the determined value with a standard sGPVI value of normal or healthy individuals, or a reference sGPVI value or a range of sGPVI values for patients of the disease to diagnose the disease, the susceptibility to the disease or the risk of developing the disease;

wherein the first and the second anti-GPVI antibodies or fragments thereof specifically bind loop 9 or loop 11 in GPVI domain 2; and loop 2 or loop 5 in GPVI domain 1.

10. The method of claim 9, wherein said disease is selected from the group consisting of angina pectoris, acute myocardial infarction, heart disease, cerebral infarction and dementia.

11. The diagnostic method according to claim 9, wherein said disease is a thrombotic disease, an embolic disease or an arteriosclerotic disease caused by vascular endothelial injury or arteriosclerosis.

* * * * *

UNITED STATES PATENT AND TRADEMARK OFFICE
CERTIFICATE OF CORRECTION

PATENT NO. : 8,323,905 B2
APPLICATION NO. : 12/225722
DATED : December 4, 2012
INVENTOR(S) : Hosaka et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 470 days.

Signed and Sealed this
Fifth Day of August, 2014

Michelle K. Lee
*Deputy Director of the United States Patent and Trademark Office*